US008840547B2

(12) United States Patent
Rivera et al.

(10) Patent No.: US 8,840,547 B2
(45) Date of Patent: Sep. 23, 2014

(54) FLEXIBLE, SELECTIVELY ROTATABLE TISSUE RETRACTOR AND METHOD FOR USING THE RETRACTOR

(75) Inventors: Carlos Rivera, Miami, FL (US); Matthew A. Palmer, Miami, FL (US); Michael Kirk, Miami, FL (US); Max Mendez, Miami, FL (US)

(73) Assignee: Syntheon, LLC, Miami, FL (US)

( * ) Notice: Subject to any disclaimer, the term of this patent is extended or adjusted under 35 U.S.C. 154(b) by 1332 days.

(21) Appl. No.: 12/329,324

(22) Filed: Dec. 5, 2008

(65) Prior Publication Data
US 2009/0137878 A1 May 28, 2009

Related U.S. Application Data

(63) Continuation-in-part of application No. 10/728,389, filed on Dec. 5, 2003, now Pat. No. 7,731,655, and a
(Continued)

(51) Int. Cl.
*A61B 1/32* (2006.01)
*A61B 17/02* (2006.01)
*A61B 17/29* (2006.01)
*A61B 17/00* (2006.01)
*A61B 19/00* (2006.01)

(52) U.S. Cl.
CPC ..... *A61B 17/0218* (2013.01); *A61B 2017/2926* (2013.01); *A61B 2017/2905* (2013.01); *A61B 17/00234* (2013.01); *A61B 2017/00867* (2013.01); *A61B 2019/4857* (2013.01); *A61B 2017/00349* (2013.01); *A61B 17/29* (2013.01); *A61B 2017/00827* (2013.01); *A61B 2017/00818* (2013.01)
USPC .......................................... 600/217; 600/206

(58) Field of Classification Search
CPC ........... A61B 17/0218; A61B 17/0643; A61B 17/0682; A61B 2017/00349; A61B 2017/00827; A61B 2017/00867; A61B 2017/00818; E21B 17/05
USPC ......... 600/217, 376, 374, 375, 104, 201, 206, 600/136, 137, 226; 606/144, 148, 119, 213, 606/139; 204/192.12; 607/128; 403/60, 78, 403/119, 164
See application file for complete search history.

(56) References Cited

U.S. PATENT DOCUMENTS

| | | | | |
|---|---|---|---|---|
| 2,108,206 A | * | 2/1938 | Meeker | 606/148 |
| 3,814,104 A | * | 6/1974 | Irnich et al. | 607/128 |
| 4,142,530 A | * | 3/1979 | Wittkampf | 607/116 |
| 5,492,119 A | * | 2/1996 | Abrams | 600/375 |
| 5,656,012 A | | 8/1997 | Sienkiewicz | |

(Continued)

OTHER PUBLICATIONS

Dictionary.com definition of integral. (n.d.). Dictionary.com Unabridged. Retrieved Oct. 6, 2011, from Dictionary.com website: http://dictionary.reference.com/browse/integral.*
International Search Report of PCT/US08/85764.

*Primary Examiner* — David Eastwood
(74) *Attorney, Agent, or Firm* — Mayback & Hoffman, P.A.; Gregory L. Mayback; Thomas Bethea

(57) ABSTRACT

A retractor for manipulating an object, the retractor includes a retractor body with proximal and distal ends, a retraction device with a head connected at the distal end of the retractor body and flexible needles of a shape memory material having a memory shape, the memory shape of the needles including a portion with an arcuate shape housed, at least partially, within the head. The retractor further includes an actuation device connected to the proximal end of the retractor body and operatively connected to the needles, the actuation device, upon actuation thereof, moving the needles out of the head and withdrawing the needles into the head and a rotation joint allowing the distal end of the retractor body and the retraction device to rotate independent of the proximal end of the retractor body.

20 Claims, 19 Drawing Sheets

Related U.S. Application Data continuation-in-part of application No. 10/252,079, filed on Sep. 20, 2002, now Pat. No. 7,033,378, said application No. 10/728,389 is a continuation-in-part of application No. 10/252,069, filed on Sep. 20, 2002, now Pat. No. 6,966,919, and a continuation-in-part of application No. 10/252,078, filed on Sep. 20, 2002, now Pat. No. 7,678,122.

(60) Provisional application No. 60/992,927, filed on Dec. 6, 2007.

(56) References Cited

U.S. PATENT DOCUMENTS

| | | | |
|---|---|---|---|
| 6,228,023 B1* | 5/2001 | Zaslavsky et al. | 600/204 |
| 6,258,064 B1 | 7/2001 | Smith et al. | |
| 2004/0193117 A1* | 9/2004 | Laufer et al. | 604/222 |
| 2004/0225194 A1 | 11/2004 | Smith et al. | |
| 2006/0016853 A1* | 1/2006 | Racenet | 227/176.1 |
| 2006/0111613 A1* | 5/2006 | Boutillette et al. | 600/136 |
| 2007/0010715 A1* | 1/2007 | Sixto et al. | 600/217 |
| 2008/0147113 A1* | 6/2008 | Nobis et al. | 606/205 |

* cited by examiner

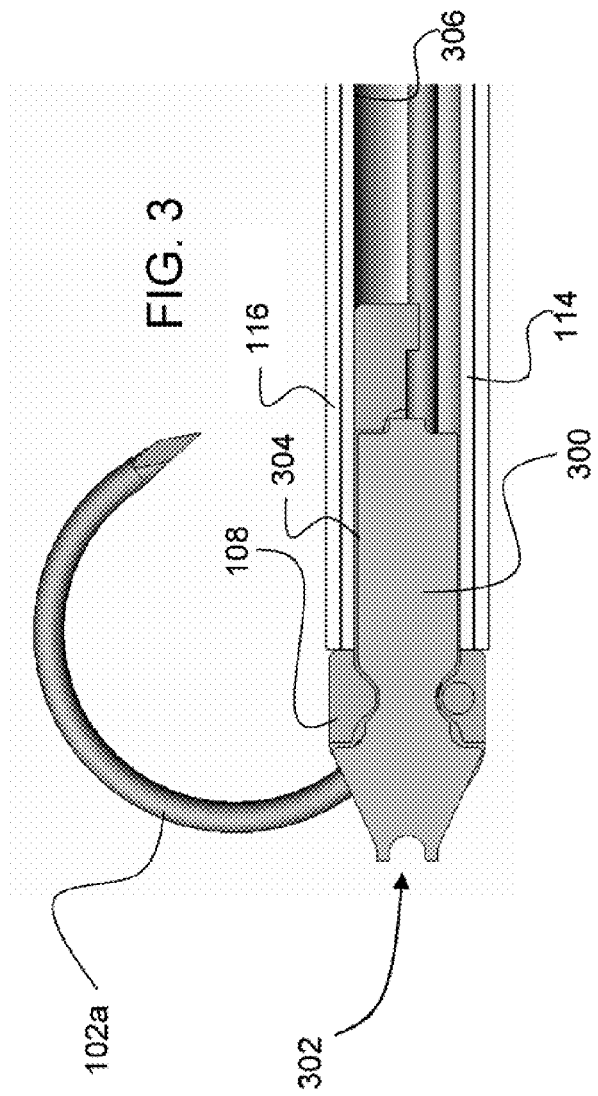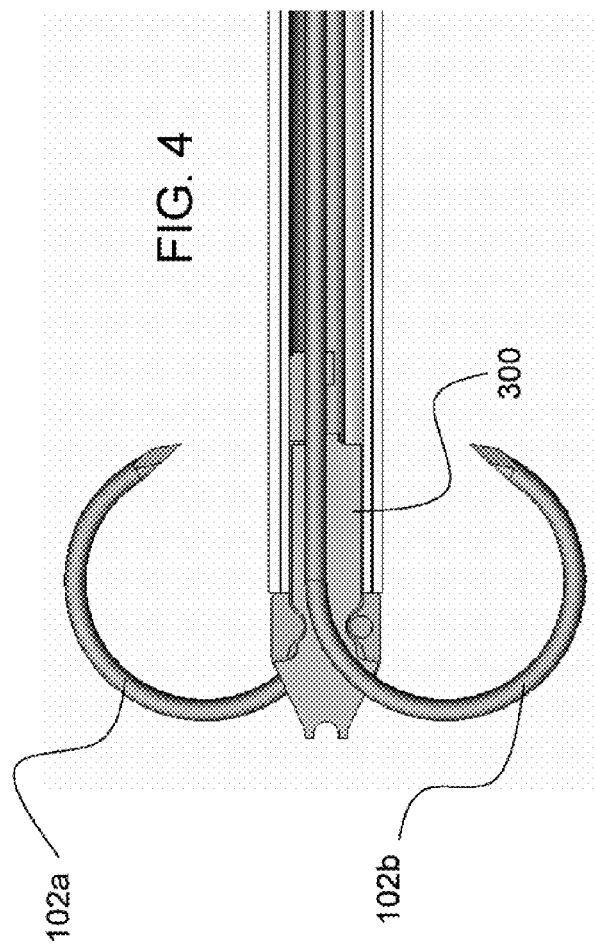

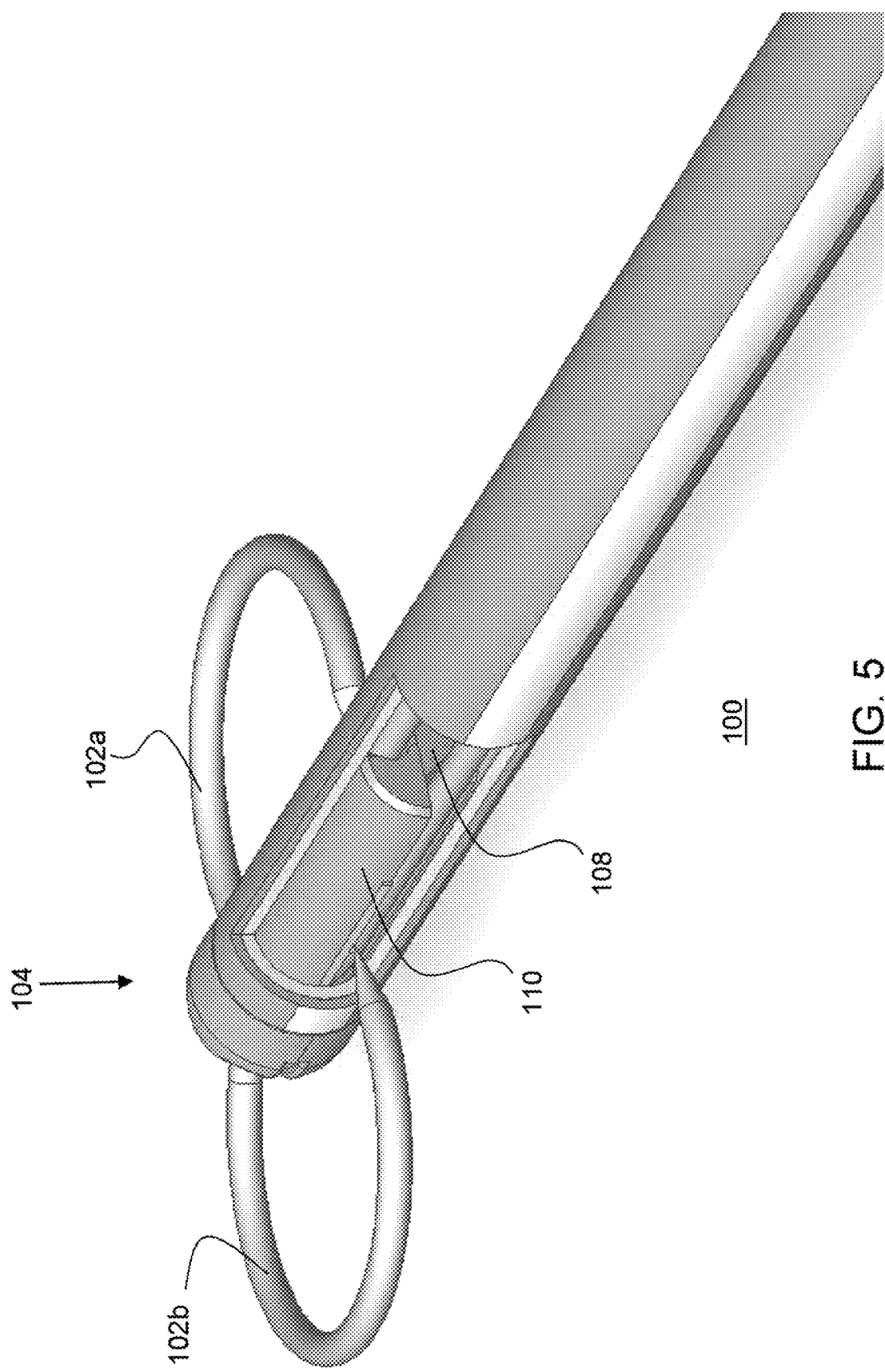

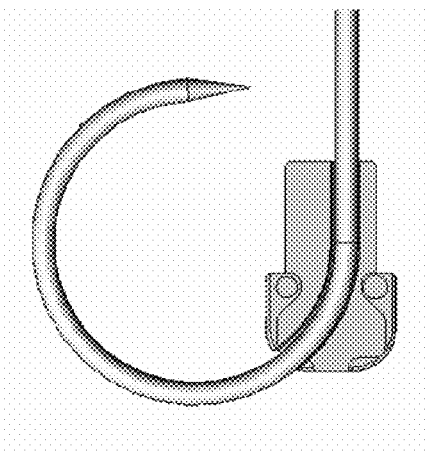
FIG. 16
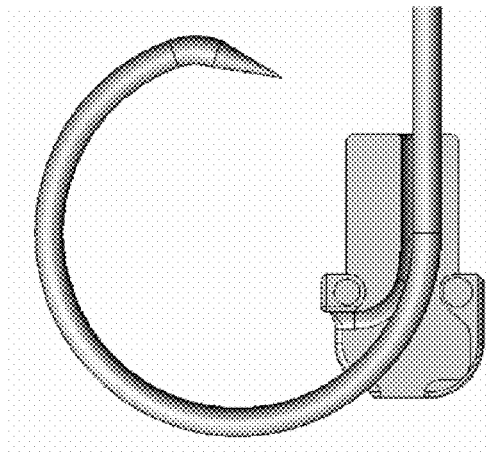
FIG. 20
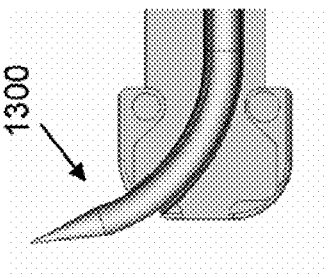
FIG. 15
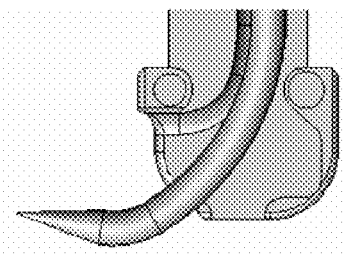
FIG. 19
FIG. 14
FIG. 18
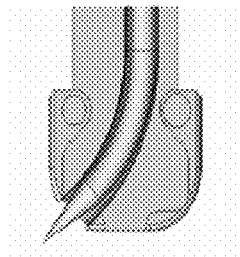
FIG. 13
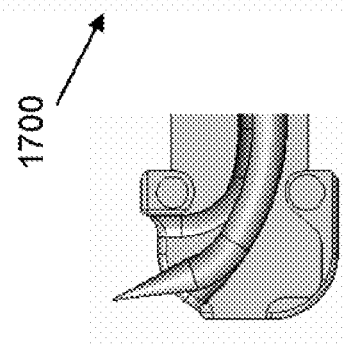
FIG. 17
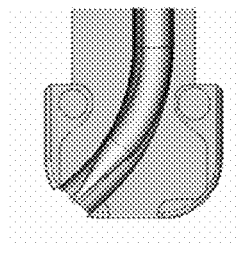

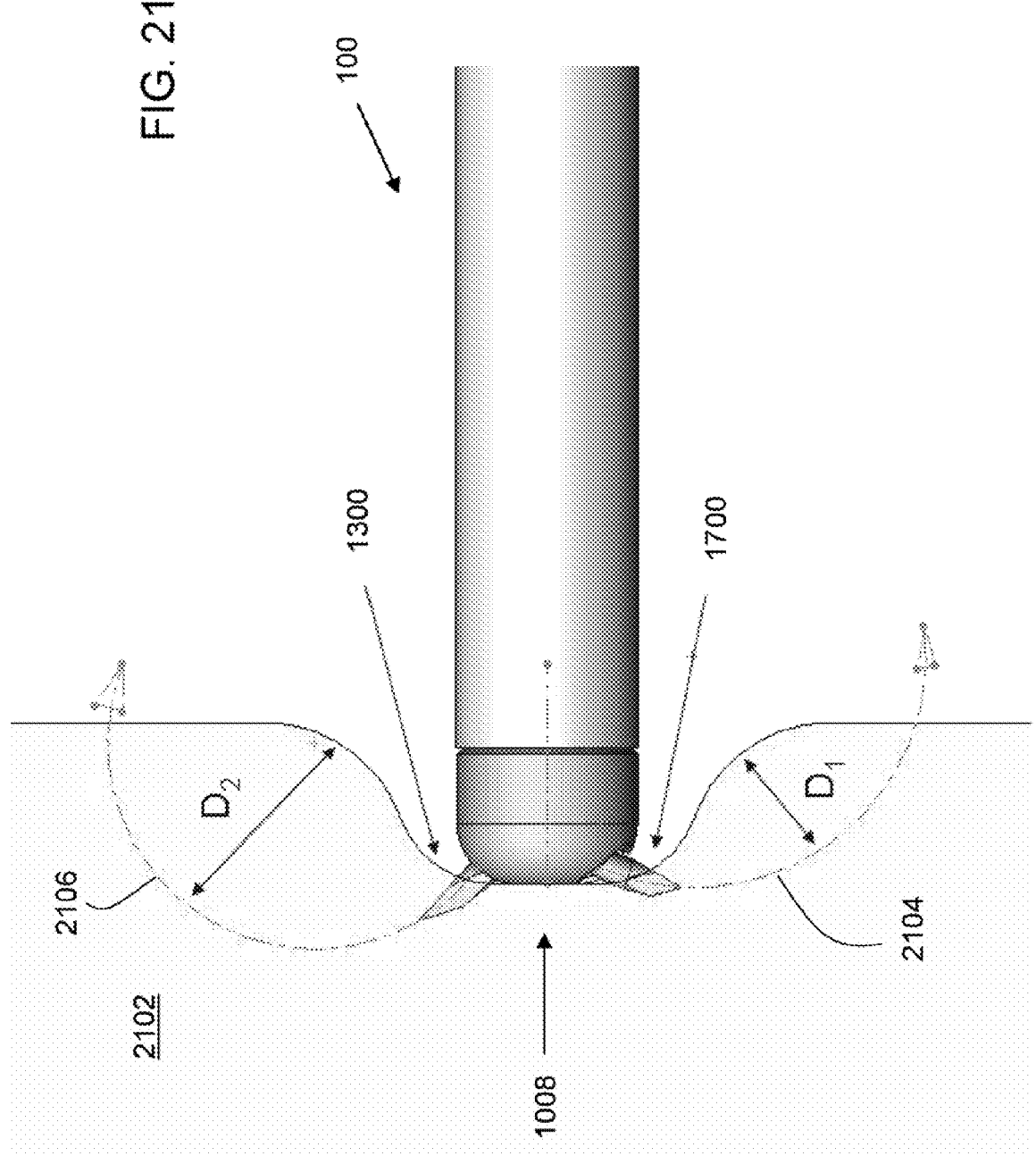

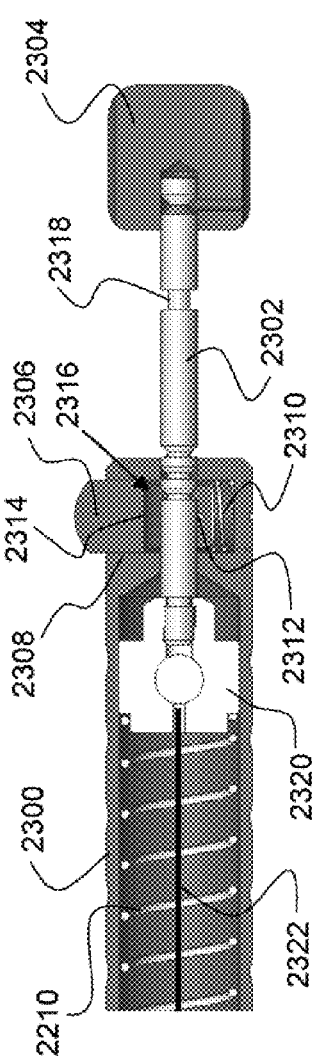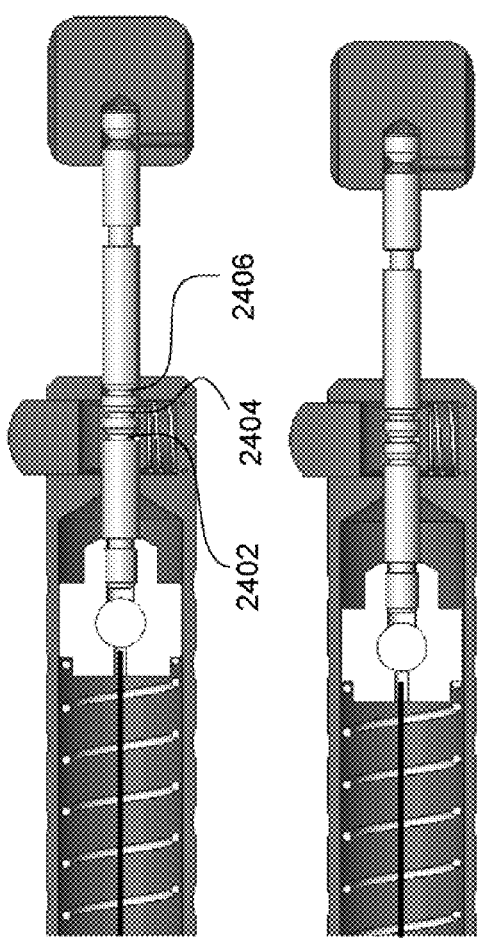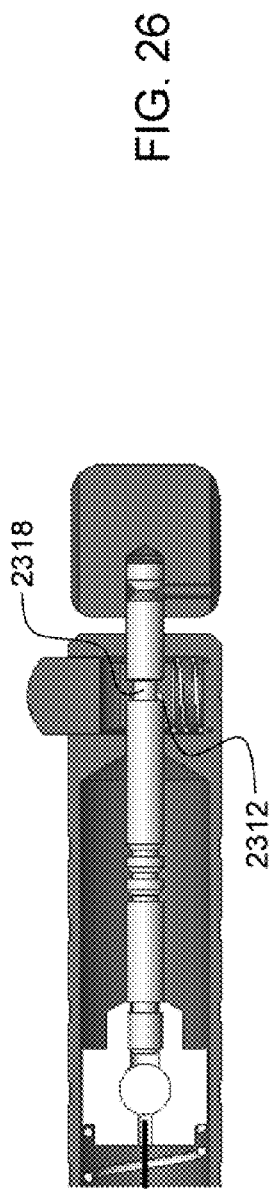

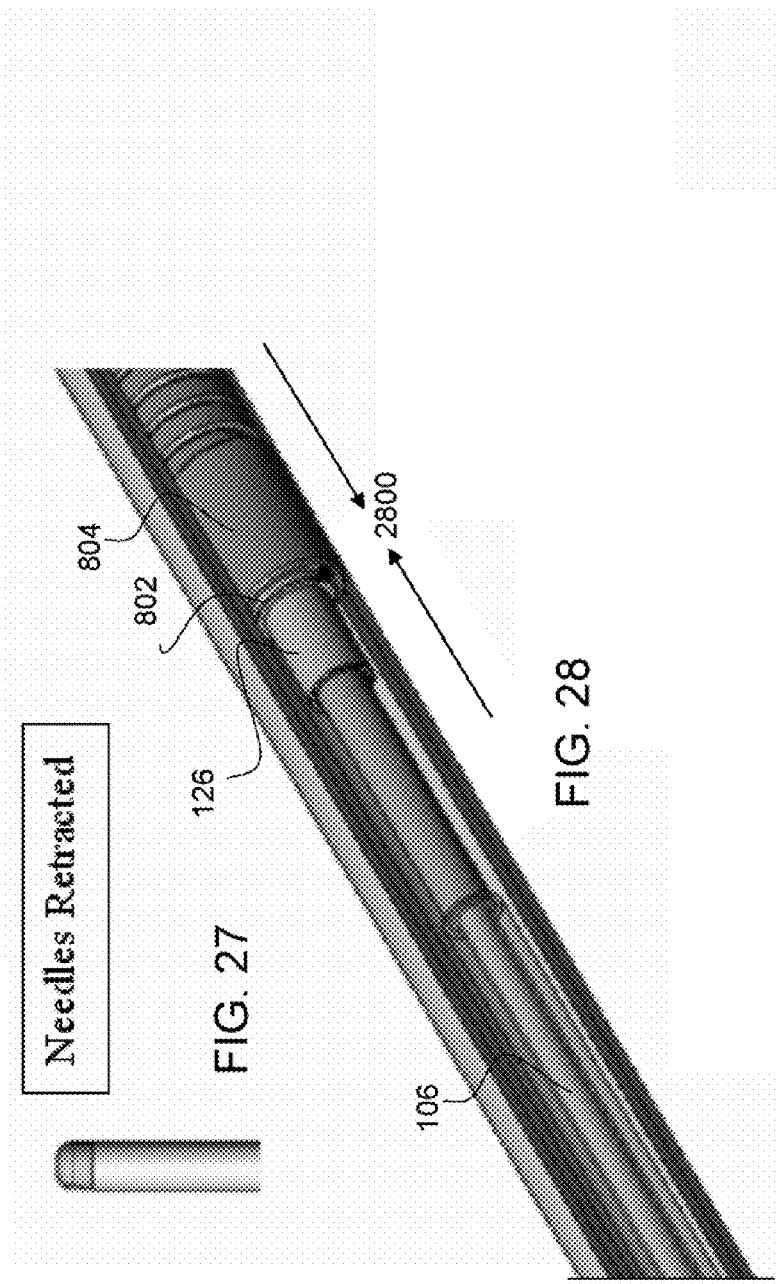

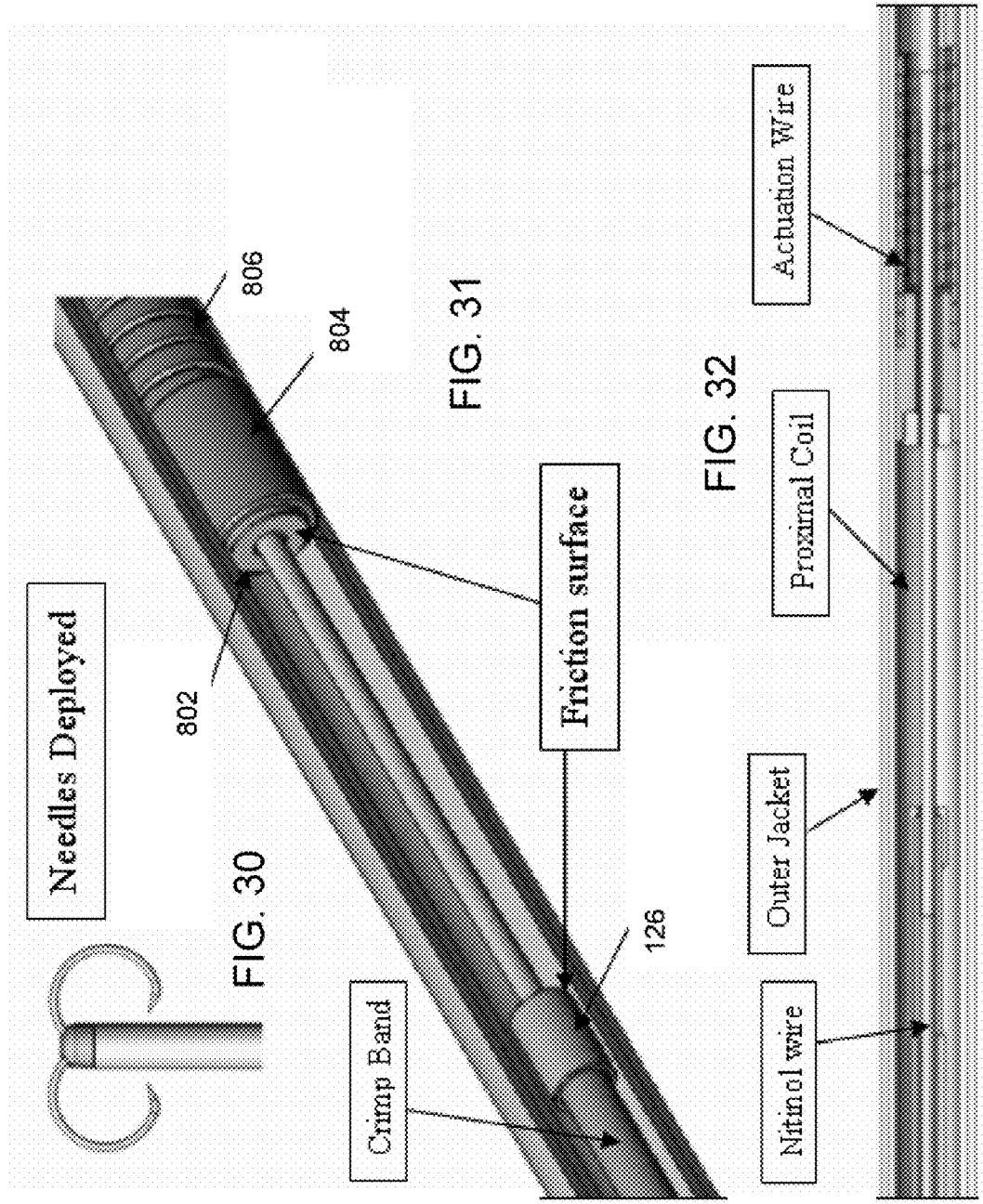

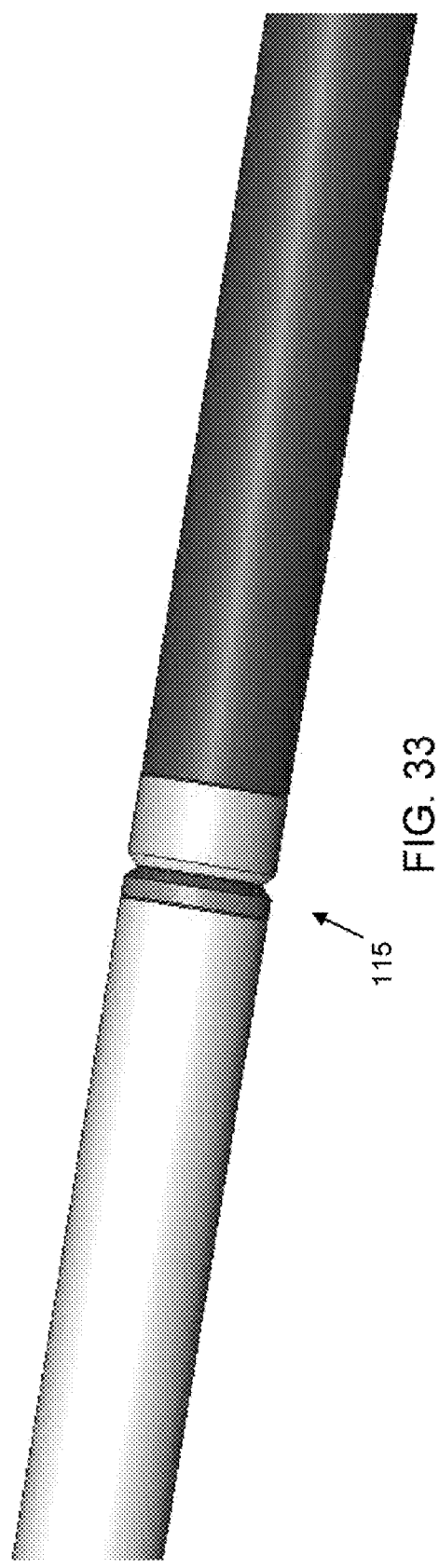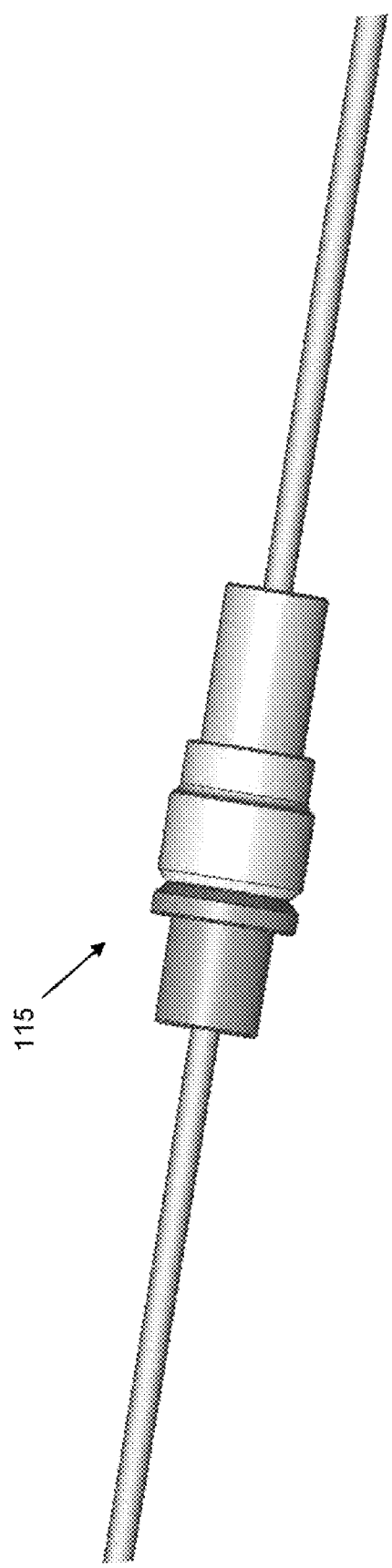

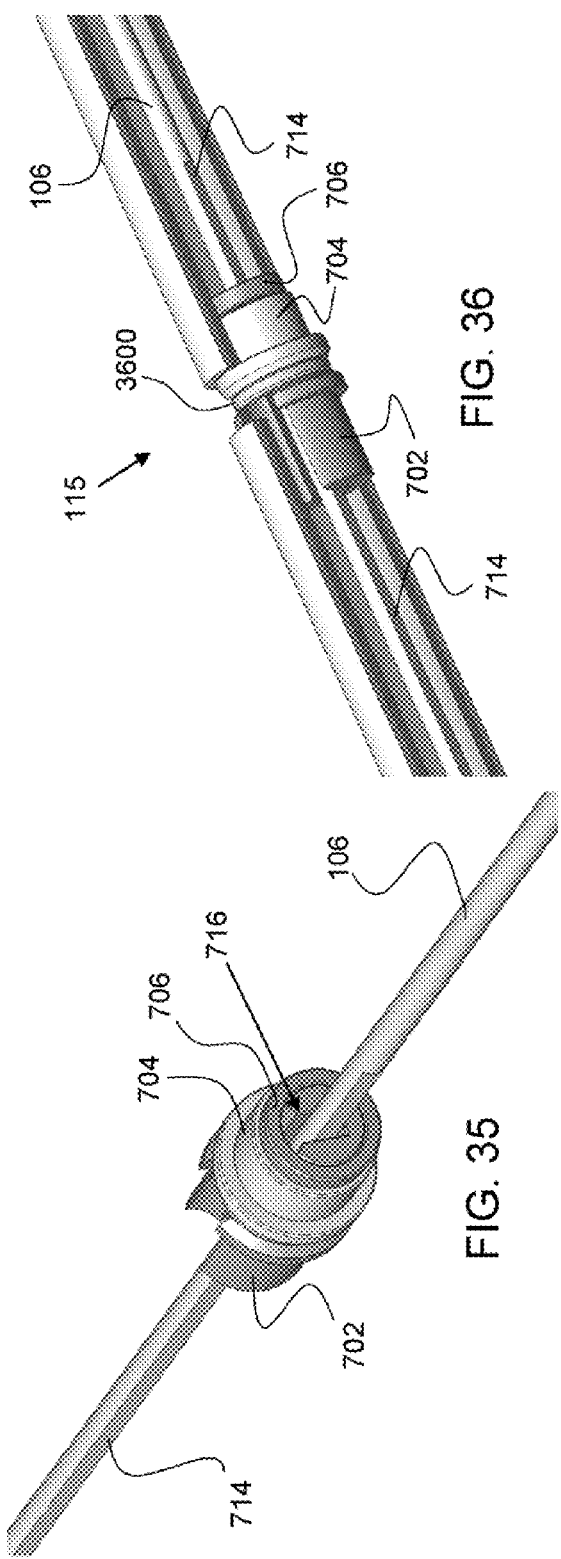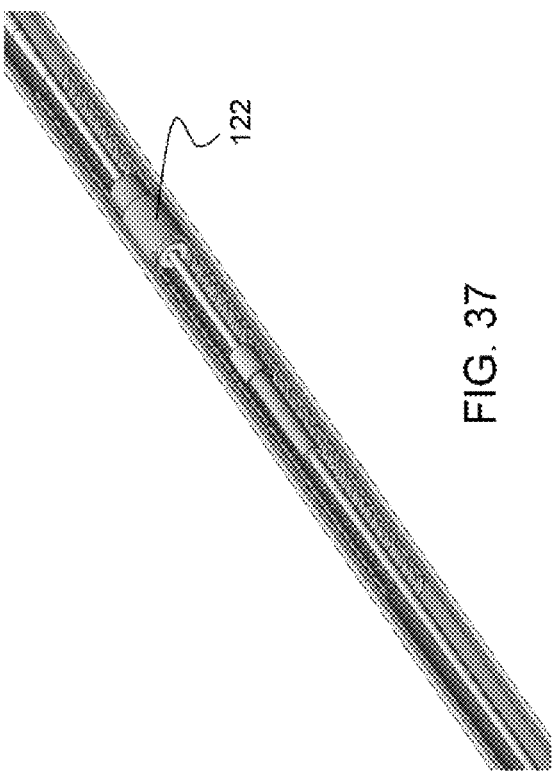

FLEXIBLE, SELECTIVELY ROTATABLE TISSUE RETRACTOR AND METHOD FOR USING THE RETRACTOR

CROSS-REFERENCE TO RELATED APPLICATION

This application:
claims the benefit under 35 U.S.C. §119(e) of U.S. provisional applications No. 60/992,927, filed Dec. 6, 2007;
is a continuation in part of copending U.S. patent application Ser. No. 10,728,389, filed Dec. 5, 2003, which claimed the benefit of U.S. Provisional Application Nos. 60/431,083, filed Dec. 5, 2002, and 60/505,009, filed Sep. 22, 2003; and
is a continuation in part of copending U.S. patent application Ser. No. 10/252,079, filed Sep. 20, 2002 and entitled "Surgical Fastener Particularly for the Treatment of Gastroesophageal Reflux Disease (GERD)," is a continuation in part of copending U.S. patent application Ser. No. 10/252,069, filed Sep. 20, 2002, and entitled "Instrument for Applying a Surgical Fastener Particularly for the Transoral Treatment of Gastroesophageal Reflux Disease (GERD)," and is a continuation in part of copending U.S. patent application Ser. No. 10/252,078, filed Sep. 20, 2002, and entitled "Method for the Surgical Application of a Fastener and the Endoluminal Treatment of Gastroesophageal Reflux Disease (GERD)."

FIELD OF THE INVENTION

The present invention relates to a tissue retractor, especially a flexible tissue retractor used as an endoscopic device that is passed through a working channel of a flexible endoscope. The tissue retractor has application in endoscopic and open surgery, including flexible endoscopy, laparoscopy, and general surgery. It can be made rigid or flexible and in lengths and diameters to suit the requirements of the surgical field. The flexible endoscopic tissue retractor is used to hold gastrointestinal tissue so that it can be retracted or manipulated in some way. The tissue retractor can be configured to allow grasping of specific layers of the gastrointestinal wall by adjusting the shape and/or length of the needles and their exit points at the tip of the device. For example it can be configured to grasp through the mucosal layer, and into the muscular layer, thus providing a more secure connection to the tissue and allowing manipulation of the entire thickness of the tissue. Alternately, it can be configured to grasp the mucosal layer allowing manipulation of the mucosal layer only.

BACKGROUND OF THE INVENTION

A number of conventional devices exist in the prior art, which devices are used to manipulate the tissue during the endoscopic surgical procedure for treatment of Gastroesophageal Reflux Disease (GERD).

For example, U.S. Pat. No. 6,494,888 B1 to Laufer et al. (referred to hereinafter as "Laufer") describes an instrument for reconfiguring stomach tissue. A tissue manipulator 700 includes an elongated cable assembly 716 and a distal end effector 718 actuated by the cable assembly 716 to perform various steps in the tissue reconfiguring procedure. See Laufer at FIGS. 9A to 9F. The end effector 718 has two jaw members 720, 722 that engage tissue, in particular, tissue at the gastroesophageal junction (GEJ). During the process of implanting the two-part fastener 732, 734 (see Laufer at FIG. 8), a coil 740 is rotated into the GEJ tissue and, after being screwed therein to a sufficient extent, is used to pull the GEJ tissue between the opening defined by the two jaw members 720, 722 in an open position illustrated, for example, in FIGS. 9D and 9E. The coil tissue puller 740, 741, 742 is shown, in particular, in FIG. 3D. The puller has certain disadvantages, however. The coil 740 can penetrate too far, causing possible negative consequences if the stomach is entirely breached (through the mucosa, muscularis, and serosa layers). Because the aorta, liver, diaphragm and other vital organs are disposed adjacent to the fundus of the stomach, if the coil 740 passes through the serosa, there is a significant chance of damage to the vital organs. Also, upon withdrawal, the coil 740, due to its inherent shape, can become stuck in the tissue and, thereby, cause damage to the tissue when the user must forcefully retract the entire assembly 718. Depending on the angle of entry, it is possible that the coil 740 only enters the mucosa. If this occurs, because the mucosa is a relatively thin, loosely attached layer, there is a high probability that the fastener 732, 734 will be only implanted in the mucosa and, therefore, result in a failed implantation procedure. Also, for fasteners that coil into the tissue, the tissue is compressed disadvantageously because rotation of the coil can twist the tissue as the coil is threaded in, which twisting can damage the tissue and cause it to weaken. Also, to advance the coil into the tissue, the coil must be rotated. It is inherently more difficult to transmit torque through a slender flexible device than it is to transmit thrust loads, thus, pushing the needles into the tissue is a more reliable actuation measure than twisting the coil into the tissue. Also, because the forces applied to the tissue by the engaging point of the device is not accompanied by an opposite reacting force of another engaging point of the device, all reaction forces must be provided through the shaft of the device.

A common general flexible endoscopic tissue grasper is most widely used today for manipulating gastrointestinal tissue (for example, one that is made by the Olympus company under the name Olympus Grasping Forceps (Catalog Number FG-49L-1)). A drawback to the Olympus grasper is its inability to reliably grasp muscularis through the mucosal layer. Another drawback is the requirement to maintain pressure on the handle while grasping the tissue. This ties up the user's hands and could lead to inadvertent release of the tissue.

The prior art devices are not constructed to easily, securely, selectively, and precisely engage the tissue during the surgical procedure.

Therefore, a need exists to overcome the problems with the prior art as discussed above.

SUMMARY OF THE INVENTION

Various endoscopic procedures require manipulation of specific layers in the gastric wall. For instance, in the case of mucosal resection, the mucosa is tented away from the muscularis and resected away. Such a procedure is currently performed by injecting fluid beneath the mucosa to, thus, lift the mucosa from the muscularis. The mucosal tissue is, then, resected using electrocautery. The tissue retractor of the present invention can be used to selectively grasp the mucosa and lift it from the muscularis, thus enabling and simplifying mucosal resection. In the case of forming a full thickness plication in the stomach, the stronger muscular layer of the gastric wall must be grasped to ensure that the full thickness of the wall will be retracted when forming the plication. By tailoring the needles and the way in which they exit from the tip of the retractor, the retractor can be made to selectively grasp the different layers in the gastric wall. Being able to grasp a specific layer of the gastrointestinal wall is advantageous depending on the requirements of the specific procedure being performed.

As it is well known, the tissue in the alimentary tract has three main layers that are, from the innermost layer to outermost layer, the mucosa, the muscularis, and the serosa. The mucosa is a relatively thin layer, loosely attached to the muscularis, and, in some procedures, retraction of only the mucosa is not desirable. For example, if the mucosa is retracted in a procedure for treatment of GERD, such retraction will not provide a sufficient plication for insertion of a GERD-treating fastener. In this exemplary procedure, retraction of entire thickness of the stomach wall is desired, as such retraction will provide a beneficial plication for insertion of the GERD fastener.

The present invention provides a rotating tissue retractor and method for using the retractor that overcome the hereinafore-mentioned disadvantages of the heretofore-known devices and methods of this general type and that can effectively grab the tissue of the alimentary tract during operation and avoid reaching into the serosa, can grab the tissue without compressing and/or tearing the tissue, and can rotate the end effector independently of the outer device shaft.

The tissue retractor of the present invention has applications in laparoscopic and general surgery as well. It can be used to retract organs that are in the way of the surgical field, or to appose and hold tissue in place during suturing. An advantage to an organ retractor or tissue apposition device according to the present invention is the ability to retain the tissue without having to clamp onto it. The tissue retractor atraumatically retains the tissue by penetrating it with fine needles and independent rotation of the end effector allows the needles to extend into the tissue in a most-desirable orientation. To further reduce the trauma to the tissue, the needles can be formed with a conical point instead of a faceted point. This is especially advantageous when retracting sensitive organs such as the pancreas. Currently available tissue graspers use more aggressive serrated articulating end effectors, which require clamping forces to retain the tissue and, therefore, potentially cause trauma in the process. The needles can also be formed with a kink in the distal end. If the kink extends towards the interior center of the curved path, then such an orientation will allow the needle to tunnel within the tissue better in the desired curved (e.g., circular) direction.

A common procedure during flexible endoscopy is the exchange of an endoscope during a procedure. If the first scope is in a position within the alimentary tract that was difficult to achieve, and it is desired that the second (exchange) scope be in the same position, the tissue retractor could be used to guide the second scope into the position of the first scope. A flexible endoscopic version of the retractor according to the present invention can be provided with a removable handle. Therefore, when a scope exchange is necessary, the tissue retractor can be passed through the first scope and deployed in the tissue at the desired location. The handle of the tissue retractor can, then, be removed. The first scope can, then, be slid over the tissue retractor shaft, leaving the retractor shaft in-place, and removed. Then, the second scope can be fed over the tissue retractor shaft, much like a guidewire, and the scope advanced to the original position. Thereafter, the shaft can be released and removed when desired.

Also, a version of the retractor can be made that allows the distal tip of the retractor to be deployed in the tissue and, then, decoupled from the main shaft. In such an embodiment, the distal tip of the device is coupled removably to the shaft and the actuation wire is coupled removably to the needles. The needles are deployed on the target tissue and the shaft of the device is pulled proximally, thus allowing the actuation wire to slip free of the needles and the tip to slide free of the shaft. The released tip being firmly attached to the tissue has application as a marker, suture attachment points for a purse string closure, a tissue apposition suture, and an anchoring point for various things such as pH probes, miniature capsule cameras, and feeding tubes.

The device and method of the present invention allows the needles to be configured such that they can be made to penetrate deep through the mucosa and into the muscularis, making a more secure attachment to the tissue, while substantially reducing the possibility of puncturing the serosa, or penetrate less deep to grasp only the mucosal layer. The present invention engages the tissue at two opposing points, so that the tissue-engaging forces of each point react against the forces of the other; the result is that there is very little reaction load transmitted to the flexible shaft of the device. This deployment of the device does not require substantial torque or thrust loads to be supplied by the shaft. The present invention provides better visibility during placement of the retractor as no jaws are used that could obscure a view of the retraction site. It is also less traumatic to the tissue than a conventional articulating grasper due to the fine diameter and non-cutting points of the needles. The handle can be released from the user's grasp after the needles have been deployed, while still maintaining a secure attachment to the tissue, which frees the user to do other tasks. The tissue retractor is separate from an endoscope but sized to fit within a working channel of the endoscope. In exemplary embodiments, the tissue retractor of the present invention has an outer diameter of 1.8 mm and 2.4 mm.

Other features that are considered as characteristic for the invention are set forth in the appended claims.

Although the invention is illustrated and described herein as embodied in a flexible, selectively rotatable tissue retractor and method for using the retractor, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

In this document, the term "longitudinal" should be understood to mean in a direction corresponding to an elongated direction of the device's shaft—between the handle and the end effector and the term "distal" should be understood to mean in a direction towards the end effector and "proximal" should be understood to mean in a direction towards the handle.

BRIEF DESCRIPTION OF THE DRAWINGS

The accompanying figures, where like reference numerals refer to identical or functionally similar elements throughout the separate views and which, together with the detailed description below, are incorporated in and form part of the specification, serve to further illustrate various embodiments and to explain various principles and advantages all in accordance with the present invention.

FIG. 3 is a fragmentary, cross-sectional, elevational view of a distal-most end of the flexible tissue retractor of FIG. 1 with a single needle and shim in place;

FIG. 4 is a fragmentary, cross-sectional, elevational view of a distal-most end of the flexible tissue retractor of FIG. 1 with both needles and a shim in place;

FIG. 5 is a fragmentary, perspective view of a distal-most end of the flexible tissue retractor of FIG. 1 with portions of the outer jacket and inner coil removed to show the needle channels formed by the tip halves;

FIGS. 13-16 are fragmentary, elevational, cross-sectional views of the needle of the flexible tissue retractor of FIG. 1 with a straight piercing tip exiting the distal tip of the device;

FIGS. 17-20 are fragmentary, elevational, cross-sectional views of the needle of the flexible tissue retractor of FIG. 1 with a bent piercing tip exiting the distal tip of the device;

FIG. 21 is a fragmentary, elevational, partially cross-sectional view of the method of using the retractor according to the invention with an unbent needle of FIGS. 13-16 and a bent needle of FIGS. 17-20;

FIGS. 23-26 are fragmentary, elevational, cross-sectional views of a handle plunger being depressed to extend the needles according to the invention;

FIG. 27 is a fragmentary, elevational view of the distal portion of the retractor of FIG. 1 with the needles retracted;

FIG. 28 is a fragmentary, perspective view of the stop section of the retractor of FIG. 1 with the needles retracted;

FIG. 29 is a fragmentary, elevational view of the stop section of the retractor of FIG. 1 with the needles retracted;

FIG. 30 is a fragmentary, elevational view of the distal portion of the retractor of FIG. 1 with the needles deployed;

FIG. 31 is a fragmentary, perspective view of the stop section of the retractor of FIG. 1 with the needles deployed;

FIG. 32 is a fragmentary, elevational view of the stop section of the retractor of FIG. 1 with the needles deployed;

FIG. 33 is a fragmentary, elevational view of the rotation joint of the retractor of FIG. 1 according to the invention;

FIG. 34 is a fragmentary, elevational view of the rotation joint of the retractor of FIG. 1 according to the invention;

FIGS. 35 and 36 are a fragmentary, perspective views of the rotation joint of the retractor of FIG. 1 showing a keyed pathway for the activation wire, according to the invention;

FIG. 37 is a fragmentary, perspective view of the retractor of FIG. 1 in a needle deployed position, according to the invention.

DETAILED DESCRIPTION

Figure 1:
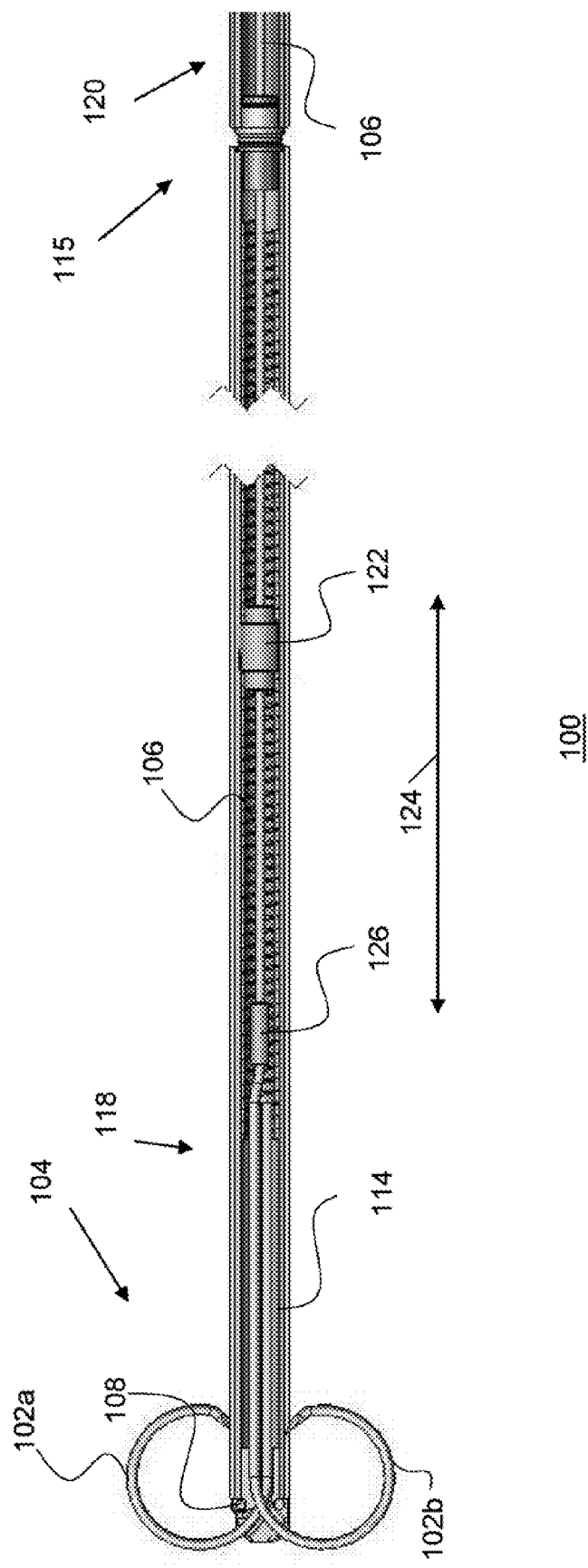
FIG. 1 is a fragmentary, cross-sectional, elevational view of a distal end of the flexible tissue retractor according to the invention with needles in a deployed position.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Referring now to the figures of the drawings in detail and first, particularly to FIG. 1 thereof, there is shown a cutaway elevational view of a flexible tissue retractor 100 with a pair of needles 102a, 102b in an extended position, according to an embodiment of the invention. The components of the retractor 100 further include, among other elements, a connector 126, a distal needle body 106, a distal stop 122, and a rotation joint 115.

In the preferred configuration, the needles 102a, 102b are made of a flexible shape memory material having a memory shape, in particular, one displaying temperature- and stress-induced martensite. The preferred material is Nitinol, a superelastic Nickel Titanium alloy having the shape memory features as described, for example, in U.S. Pat. Nos. 4,665,906, 5,067,957, and 5,597,378 to Jervis. The needles 102a, 102b are formed to have the memory shape shown in FIGS. 1 to 6 at least at room and body temperature, in particular, above approximately 10° C.

The connector 126 shown is a sleeve that can be squeezed by a mechanical stress to be fixedly connected to a needle body 106 of one of the needles, 102b in this example. Alternatively, the connector 126 can be a heat-contacted sleeve in which heat welds, forms, molds, or otherwise shapes the body of the connector 126 to affix the connector 126 to the body of the needle 102b. The straight body section of the other needle 102a can be coupled to the first needle 102b by any available method, such as welding.

Figure 2:
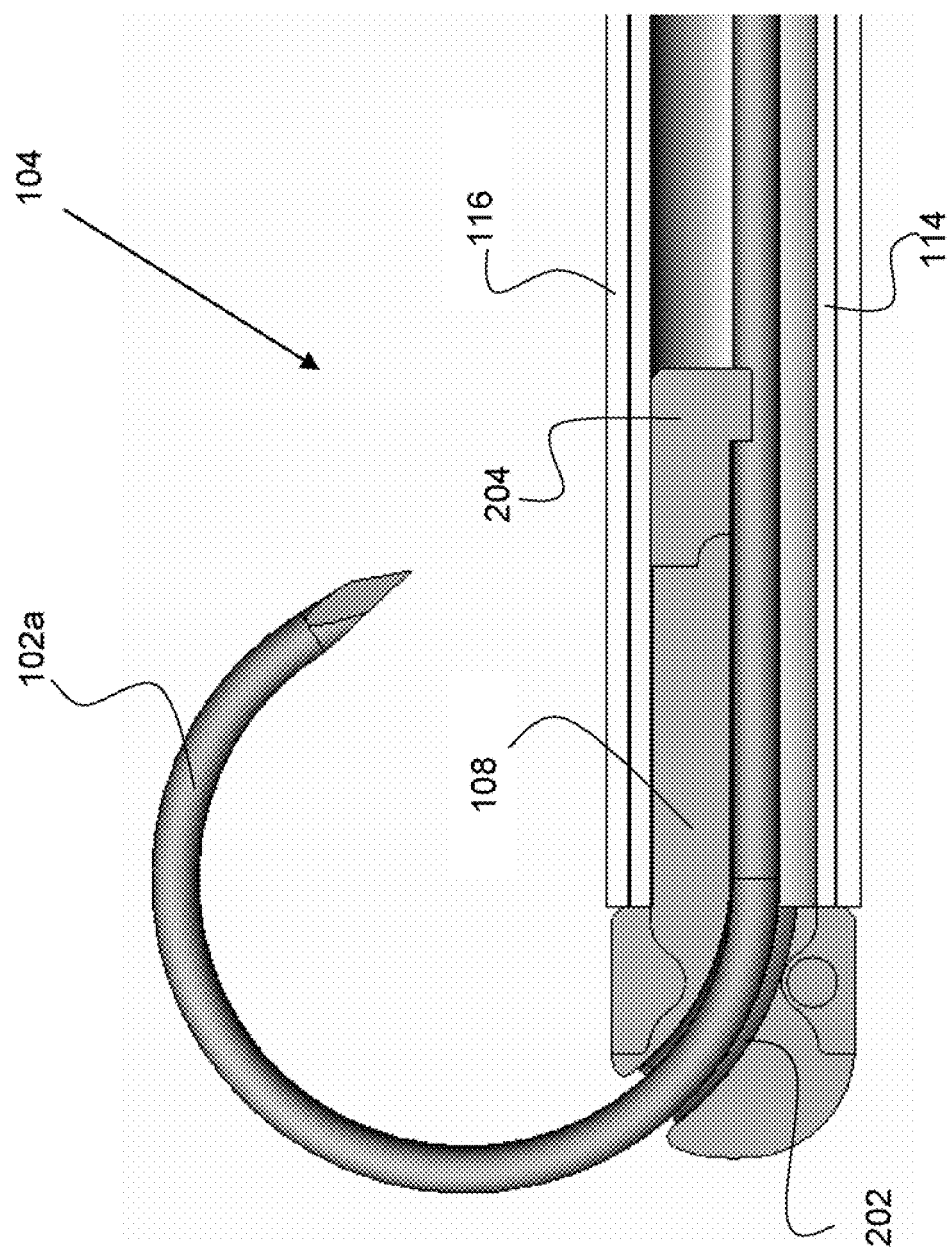
FIG. 2 is a fragmentary, cross-sectional, elevational view of a distal-most end of the flexible tissue retractor of FIG. 1 with a single needle in place.

FIGS. 2-4 show enlarged cutaway views of the head 104 of the retractor 100. Referring first to FIG. 2, a first 108 of two head halves 108, 110 (110 not shown in this view) is surrounded and secured by the distal coil winding 114, which, in turn, is surrounded by an outer jacket 116. The first head half 108 has a channel 202 that receives and guides a first 102*a* of the two needles 102*a*, 102*b* out of the retractor 100 when the needles 102*a*, 102*b* are deployed, as is the case in FIGS. 1-4. In one embodiment of the present invention, the first head half 108 also has an end 204 that partly surrounds the needle 102*a* and, when combined with the second head half 110, creates channels that provide guidance to the needles 102*a*, 102*b* and ensures that the needles 102*a*, 102*b* each travel along individual paths without interfering with each other.

In FIG. 3, a shim 300 is placed over the first head half 108 and the first needle 102*a*. The shim 300 serves three functions. A first function is covering the top of the channel 202 and preventing the first needle 102*a* from leaving the channel 202. A second function is to separate the needles 102*a*, 102*b* from each other. Thirdly, the shim 300, as can be seen in FIGS. 3 and 4, has an end 302 that extends longitudinally out of the retractor head 104. The shim end 302 has a shape and, as will be shown below, can be any of a variety of shapes that serve various functions and provide a variety of advantages.

FIG. 4 shows the second needle 102*b* placed within the flexible tissue retractor and separated from the first needle 102*a* by the shim 300. As set forth above, the shape memory of the needles 102*a*, 102*b* imparts a force to whatever structure is preventing the needles 102*a*, 102*b* from being in the defined memory shape. This force also imparts a torque upon the needles 102*a*, 102*b* when the needles 102*a*, 102*b* are at least partially deformed by being retracted into the channel 202 in the head halves 108, 110. The imparted torque, if left unchecked, would move the needles 102*a*, 102*b* out of the channel 202. Without the shim 300, therefore, the two needles 102*a*, 102*b* would twist around one another and possibly jump into the other needle's respective groove. To prevent such movement, and to insure that each of the needles 102*a*, 102*b* stay within its respective channel 202, the shim 300 is disposed between the two needles 102*a*, 102*b*. In such a position, a flat version of the shim 300 forms an interior first bearing surface for each of the needles 102*a*, 102*b* and the channel 202 forms an almost circular exterior second bearing surface for each of the needles 102*a*, 102*b*. Alternatively, the shim 300 can have a non-illustrated depressed hemispherically cross-sectioned groove corresponding to the channel 202 on each of the head halves 108, 110. Thus, the channel 202 need not so deeply penetrate the head halves 108, 110.

The shim 300 has other significant features. First, as shown in FIG. 3, the distal-most end 302 of the shim 300 can have an anchoring shape. The function of the anchoring shape is to keep the end 302 in place and prevent the end 302 from glancing off a tissue surface (i.e., human tissue, in particular, the wall of the stomach) when the tip 302 of the tissue retractor 100 is pushed initially against the tissue surface. It is noted that the tissue surface is compressed therein and around the shaped end 302 to secure the retractor 100 at a grasping location on the surface and prevent radial movement with respect to the shaped end 302. In one embodiment, the end 302 of the shim 300 is provided with a soft material, such as cotton, which absorbs liquid as well as provides a soft contact area to be placed against tissue. The soft material resists movement of the device 100 with reference to the tissue that it is in contact with, as well as avoids any tissue damage.

In a mechanically efficient manner, the shim 300 can be provided with non-illustrated thread points 304 having a pitch equal to, or slightly different than, a pitch of an interior non-illustrated female thread 306 of the distal coil winding 114. Accordingly, when the tip is entirely assembled with the shim 300 and needles 102*a*, 102*b*, the thread points 304 can be used as a male thread to secure the tip in the distal end of the distal coil winding 114.

Figure 6:
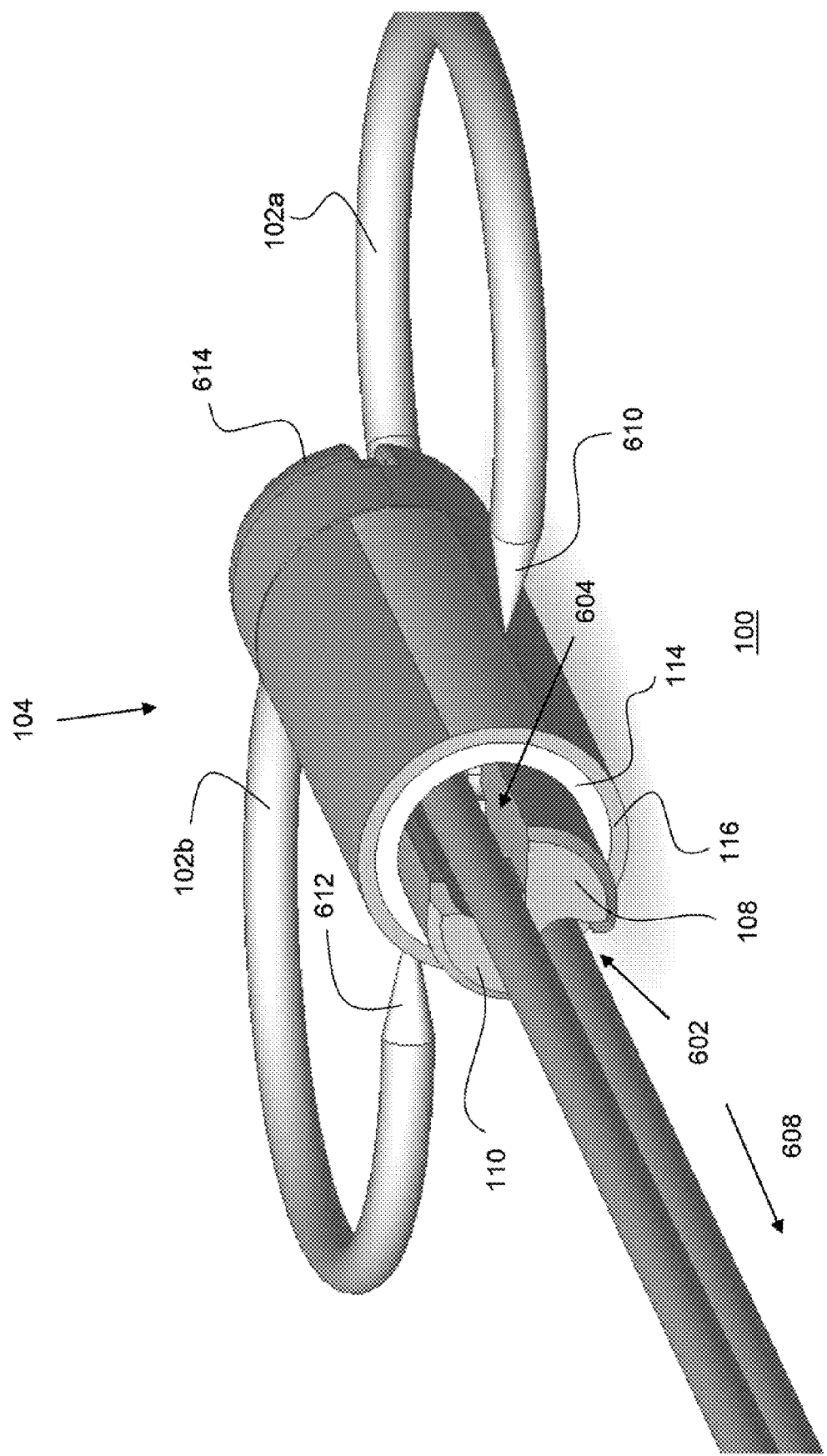
FIG. 6 is a fragmentary, perspective view of the distal-most end of the flexible tissue retractor of FIG. 5 with larger portions of the outer jacket and inner coil removed to show the needle channels formed by the tip halves.

FIG. 5 shows a partially cutaway perspective view of the retractor 100 with both head halves 108, 110 at the head 104 and securing the two needles 102*a*, 102*b*. The view of FIG. 5 clearly shows the two separate paths that the head halves 108, 110 provide to the needles 102*a*, 102*b*. FIG. 6 provides another perspective view of the head 104 of the retractor 100 with the head halves 108, 110 accommodating and securing the needles 102*a*, 102*b* in channels 602, 604, respectively. Thus, when the needles 102*a*, 102*b* are moved proximally, the bodies of the needles 102*a*, 102*b*, respectively, are guided through the channels 602, 604, respectively, and straightened when exiting the channels 602, 604 in a proximal direction, indicated by arrow 608. With further proximal movement, the needle tips 610, 612 are, ultimately, fully retracted into the channels 602, 604.

Referring again briefly to FIG. 1, a distal stop 122 is shown within the distal section 118 and downstream from the proximal section 120. Generally speaking, the distal stop 122 prevents the needle tips 610, 612 (shown in FIG. 6) from completely exiting the proximal end of the head halves 108, 110 and, thereby, rendering the flexible tissue retractor 100 inoperable. The reason why the retractor 100 would be rendered inoperable is because of the unique nature of the needles 102*a*, 102*b*. Thus, if the needle tips 610, 612 are retracted past a proximal end surface 614 of the head halves 108, 110, the needle tips 610, 612 would spring towards their memory shape and completely out of the grooves 602, 604 to rest inside the distal coil winding 114. In such a position, the bias provided by the shape memory would substantially prevent the retractor 100 from being operated, at least until the retractor 100 was disassembled, fixed, and, thereafter, reassembled. As will be explained in more detail below, the stop 122 is laterally fixed to the winding coil 114. As the body 106 of the needle 102*b* moves proximally in a lateral direction 124 through the stop 122, the distance between the connector 126 and the stop 122 will reduce until the two make contact. At that point, the needles cannot move any further in the proximal direction.

Still referring to FIG. 1, it can be seen that a rotation joint 115 rotatably couples the distal section 118 to a proximal section 120. Through the rotation joint 115, a manipulation at the proximal end of the proximal section 120 advantageously controllably rotates the needles 102*a*, 102*b* to, for instance, perform surgical functions during a medical procedure. Details of the rotation joint 115 will now be described in conjunction with FIG. 7.

Figure 7:
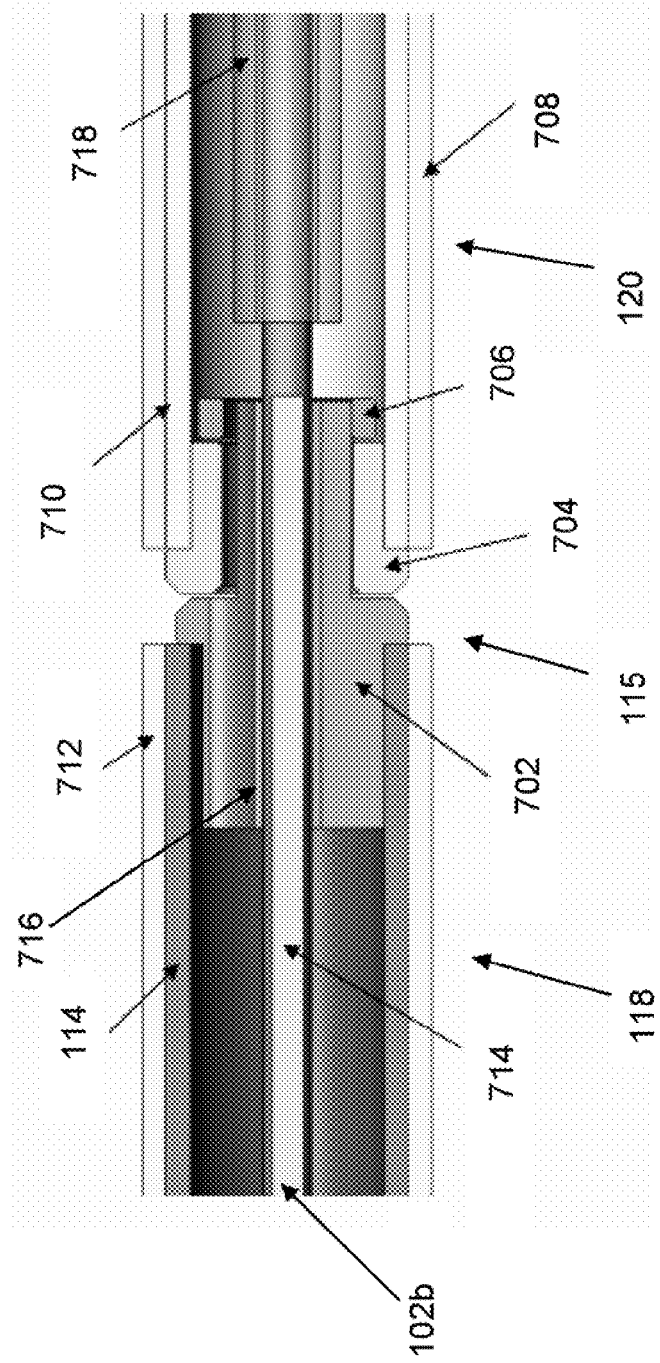
FIG. 7 is a fragmentary, elevational, cross-sectional view of a rotation joint of the flexible tissue retractor of FIG. 1.

FIG. 7 shows a cutaway partial view of the retractor 100 and, in particular, the rotation joint 115. The rotation joint 115 includes a swivel bushing 702 that is nested within a swivel coil coupler 704 and swivel bushing stop 706. Surrounding the swivel bushing 702 is the distal coil winding 114, which is itself surrounded by a distal outer jacket 712. The distal coil winding 114 securely fixedly holds the swivel bushing 702 so that a rotation of the swivel bushing 702 results in a corresponding 1:1 rotation of the distal coil winding 114. Similarly, a proximal coil 710 securely fixedly holds the swivel coil coupler 704 so that a rotation of the swivel coil coupler 704 results in a corresponding 1:1 rotation of the proximal coil 710. A proximal outer jacket 708 surrounds and protects the proximal coil 710.

Figure 9:
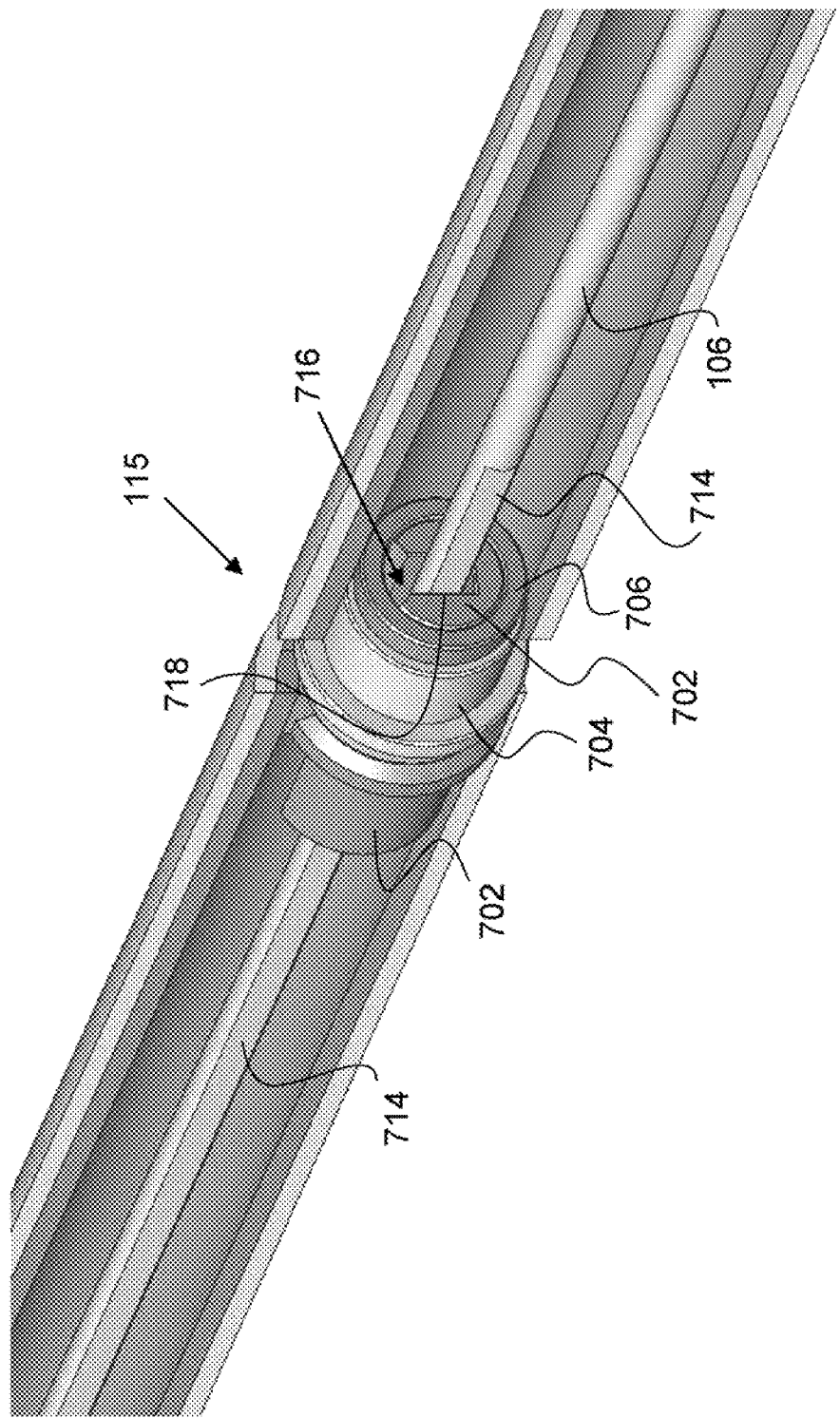
FIG. 9 is a fragmentary, perspective, partially cross-sectional view of the rotation joint of the flexible tissue retractor of FIG. 1.

The body of the needle 106 passes from the proximal section 120 to the distal section 118 through the rotation joint 115 and it is this needle body 106 that causes the rotation of the distal section 118 relative to the proximal section 120 during a surgical procedure. According to one embodiment of the present invention, the wire passes through slot 716 in the swivel bushing 702. The slot 716 provides at least one engaging surface 718 for the needle body 106 to align with. In this example, the slot 716 is not round, but is instead a groove or resembles an ovular shape with flat opposing side walls 718. This slot can better be seen in FIG. 9. The needle body 106 is also provided with at least one engaging surface 714, which, in this example, is a flat edge that, once inserted into the slot 716, prevents rotation of the needle body 106 independent of the swivel bushing 702. As previously stated, the swivel bushing 702 rotates independent of the swivel coil coupler 704. As a result, when the distal outer jacket 712, which is fixedly coupled to the swivel coil coupler 704 by the proximal coil 710, is rotationally fixed, and the needle body 106 is rotated with respect to the outer jacket 712, the keyed coupling between the flattened section of the needle body 106 and the slot 716 in the swivel bushing 702 causes the swivel bushing 702 and affixed distal coil winding 114 and proximal outer jacket 708 to rotate as well. This keyed relationship between the needle body 106 and the swivel bushing 702 can also be seen in FIGS. 35-36.

FIG. 7 also shows that, on the proximal side of the rotation joint 115, the needle body 106 is wrapped in a sheath 718, preferably, of polyethylene or TEFLON®. Because there is a difference between the outer diameter of the needle body 106 and the inner diameter of the coil winding 114, when pushed against a load, the needle body 106 may flex and bend. The sheath 718 fills the space between the outer diameter of the needle body 106 and the inner diameter of the coil winding 114 and prevents the needle body from flexing or buckling. In addition, the sheath 718 also insolates the needle body 106 from the proximal coil 710 and allows the needle body 106 to rotate within the proximal section 120 with limited resistance.

Figure 8:
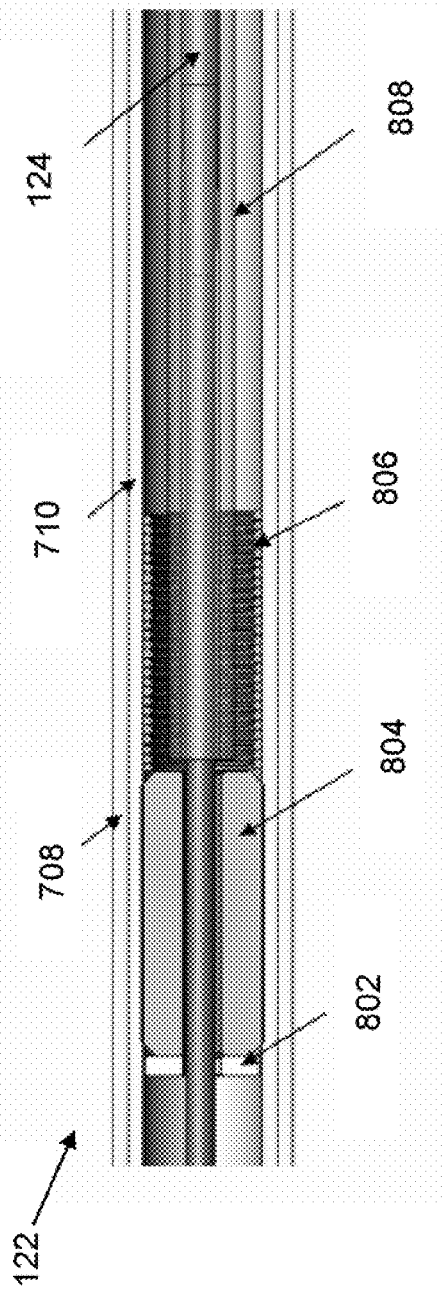
FIG. 8 is a fragmentary, elevational, cross-sectional view of a proximal stop of the flexible tissue retractor of FIG. 1.

Continuing further along the flexible tissue retractor 100, the needle body 106 passes through the proximal stop section 122, as shown in FIG. 8. The proximal stop section 122 includes a bushing 802, a proximal stop 804, and a strain relief coil 806, which are all fixedly secured to the proximal coil 710. In addition, an actuation wire inner sheath 808 surrounds the proximal needle body 106. The proximal stop section 122 provides a lateral motion limit to the needle body 106 and is positioned so that the needles 102a, 102b can be fully retracted into the head 104, but cannot be retracted beyond the proximal extent of the needle channels 602, 604. Specifically, as is shown in FIG. 28, when the needle body 106 is pulled away from the head 104 of the flexible tissue retractor 100, the distal stop 122 will make contact with the bushing 802, supported by the proximal stop 804. The contact between the laterally sliding distal stop 122 and the fixed bushing 802 resting against the proximal stop 804 prevents any further sliding of the distal needle body 106 in the proximal direction.

Looking back to FIG. 8, the stop 804 is hollow to accommodate the needle body 106 slidably therein (in a preferred embodiment, the sheath 808 is not allowed to pass through the stop 804). Thus, the internal diameter of the stop 804 is at least slightly greater than the external diameter of the needle body 106. In one embodiment, the stop 804 is provided with a male thread on its external surface. A groove is provided at the distal end of the stop 804, the groove, preferably, being shaped to accommodate the working end of a flat-head screwdriver for insertion within the male threads of the stop 804.

The strain relief coil 806 prevents severe bending of the proximal coil 710 to an extent where the needle body 106 would get bent or be unable to slide laterally through the stop 122.

Figure 10:
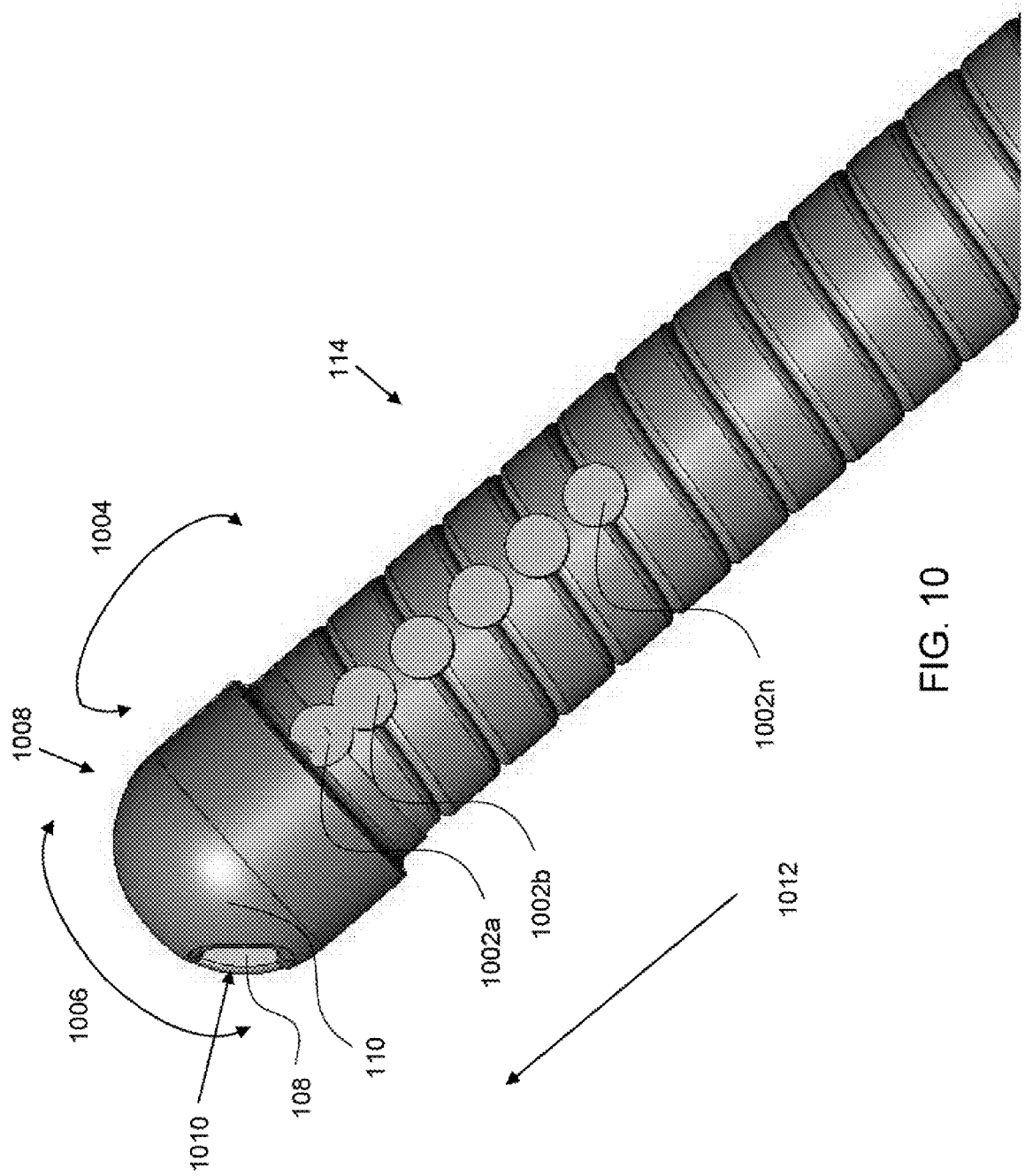
FIG. 10 is an elevational fragmentary view of a distal end of the flexible tissue retractor of FIG. 1 according to the invention with spot welds on the distal coil.

Referring now to FIG. 10, the distal coil winding 114 is made in the fashion of a tight spring, to provide it with longitudinal strength while having slight longitudinal expandability/give and to provide it simultaneously with radial flexibility or whip. Due to such coiling, the interior of the distal coil winding 114 has a natural female thread which securely holds the head halves 108, 110. In addition, spot welds 1002a-n are provided on opposing sides of the distal coil winding 114. The spot welds 1002a-n serve as winding coupling points and provide longitudinal rigidity to the coil winding 114 and prevents the individual windings from separating laterally. This is advantageous, since the outer jacket 116 terminates at this distal end and support from the jacket is minimized at this point. The welds also provide torsional rigidity in a first direction 1004, while allowing flexibility in a second direction 1006. Specifically, the welds 1002a-n prevent expansion or separation of the coils in the direction 1012 and 1004, but act as pivots in the direction 1006 and allow the coils to slightly separate. This restriction in flexibility is also advantageous during surgical procedures as it allows the operator to rotate the distal end of the device 100 to position the welds 1002a-n in a particular orientation to navigate particular channels where prevention of bending is preferred.

The tip 1008 can be made from a thin walled deep drawn part with a rounded end to maximize the internal diameter of the tip 1008, thus allowing for arcuate needles of greater chord height (shorter, smaller radius) to fit within. The exit windows 1010 for the needles 102a, 102b can be pierced through the wall as part of the deep drawing operation or machined through using various methods including at least one of: wire EDM, laser, conventional milling, etc.

Figure 11:
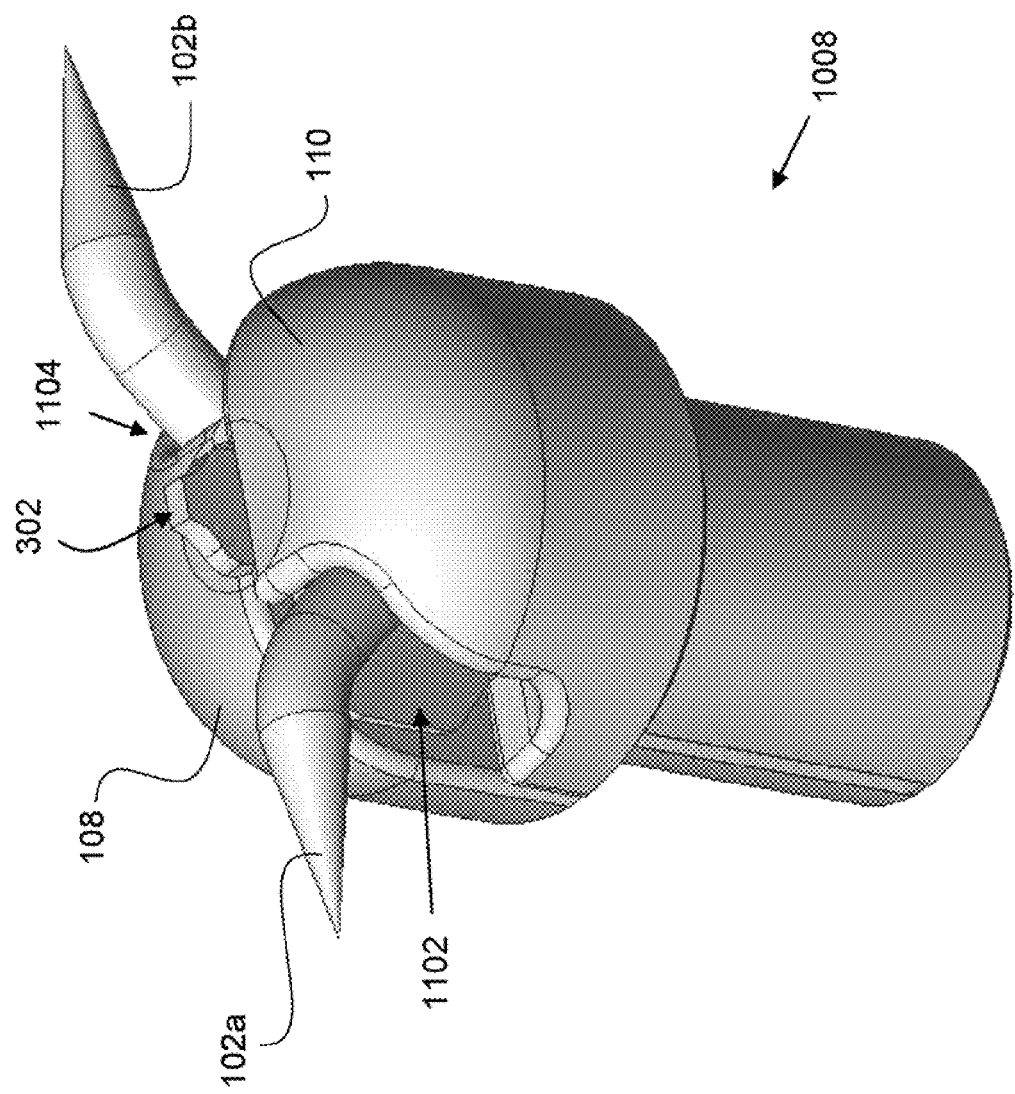
FIG. 11 is a fragmentary, perspective view of components at a distal portion of the retractor of FIG. 1.
Figure 12:
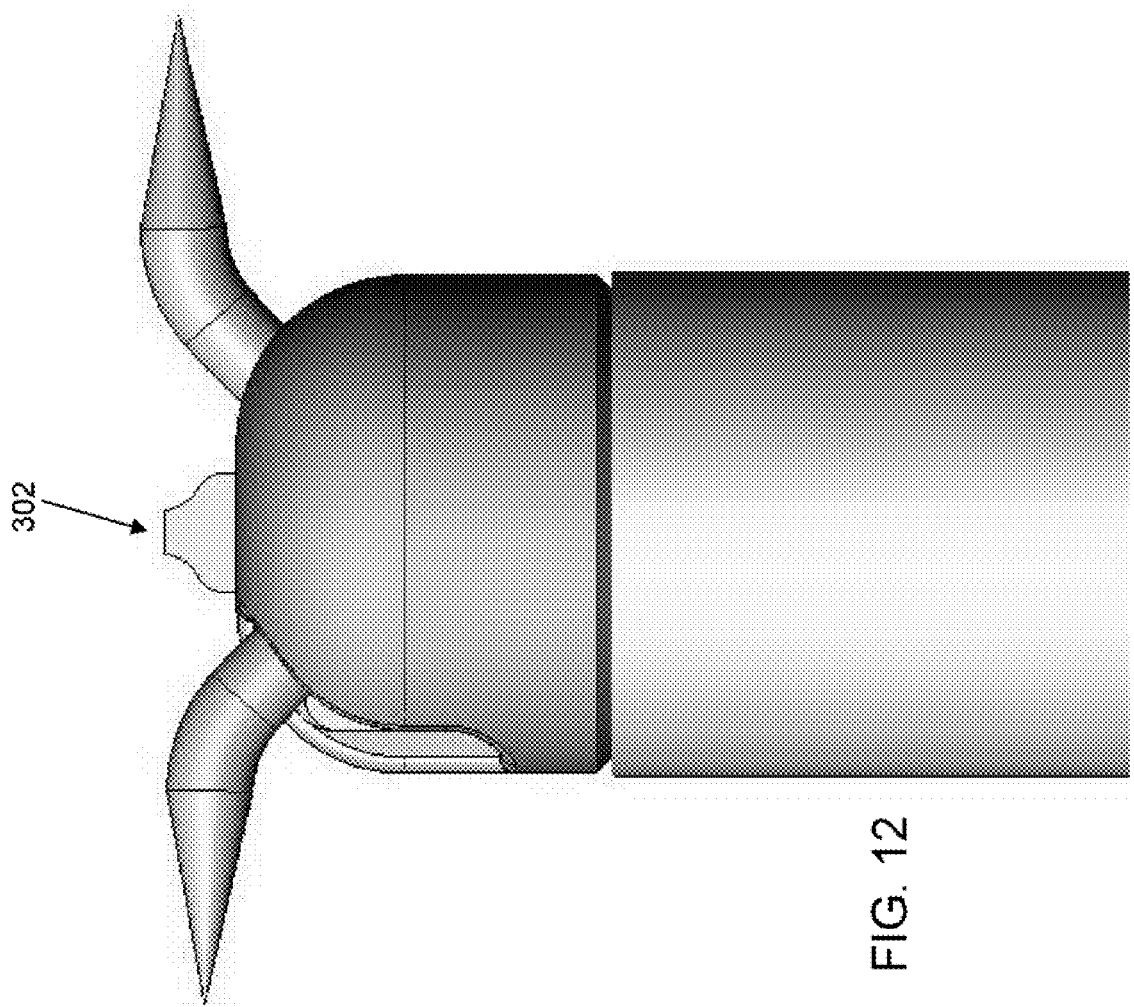
FIG. 12 is a fragmentary, elevational view of components at a distal portion of the retractor of FIG. 1.

As can be seen from FIG. 11, the needles 102a and 102b pass through openings 1102, 1104 on the distal tip 1008 to extend out of the distal tip 1008. To explain the movement of the needles 102a, 102b through the tip 1008, FIGS. 13 to 20 show different views of the needles 102a, 102b, which can move between a retracted position (FIGS. 13 and 17) and a fully extended position (FIGS. 16 and 20). The entirety of such movement is referred to as selective movement because actuation of the needles is selected by a user anywhere between (FIGS. 14, 15, 18, and 19) the fully retracted and fully extended positions.

FIGS. 13-16 show a needle tip 1300 with a bend that is different from the bend angle of the needle tip 1700, shown in FIGS. 17-20. More specifically, needle tip 1700 is bent at a greater natural angle of curvature than is needle tip 1300. The effect of each of these exemplary needle tips is shown in FIG. 21 and explained below.

In a preferred embodiment, the flexible tissue retractor 100 is an endoscopic device that is passed through the working channel of a flexible endoscope. In such a procedure, as shown in FIG. 21, the retractor 100 is used to hold esophageal or any other gastrointestinal tissue 2102 so that it can be moved or manipulated in some way. As the retractor 100 is passed through one of the working channels of an endoscope, the needles 102a, 102b are in a fully retracted position in the tip 1008, as shown in FIGS. 13 and 17. Once the tip 1008 is set into place, it is pushed against the tissue 2102. Preferably, the shim 300 (not shown in FIG. 21) has the anchoring shaped end 302 (see FIGS. 3, 4, 11, and 12) to help pinpoint a desired location on the tissue and place the tip 1008 at the desired location. The needles 102a, 102b are then actuated to extend out of the tip 1008 and pierce the tissue 2102. As the needles 102a, 102b extend into and curl around the tissue 2102, it is retained securely by the shaped end 302. Now, the tissue 2102 can be manipulated as required. To release the tissue 2102, the needles 102a, 102b need merely be retracted back into the tip 1008. Because the needles 102a, 102b, made of a shape memory alloy such as nitinol, are pre-formed into the arcuate memory shape, they retain the memory shape through repeated retractions/deployments.

The needle paths 2104 and 2106 shown in FIG. 21 illustrate the difference between a needle tip 1700 with a distal end bend and a needle tip 1300 without the bend or with a shallower bend on the same device (for illustration) to show that the needle tip 1700 with the bend creates a shallower (D1) tunneling path.

Figure 22:
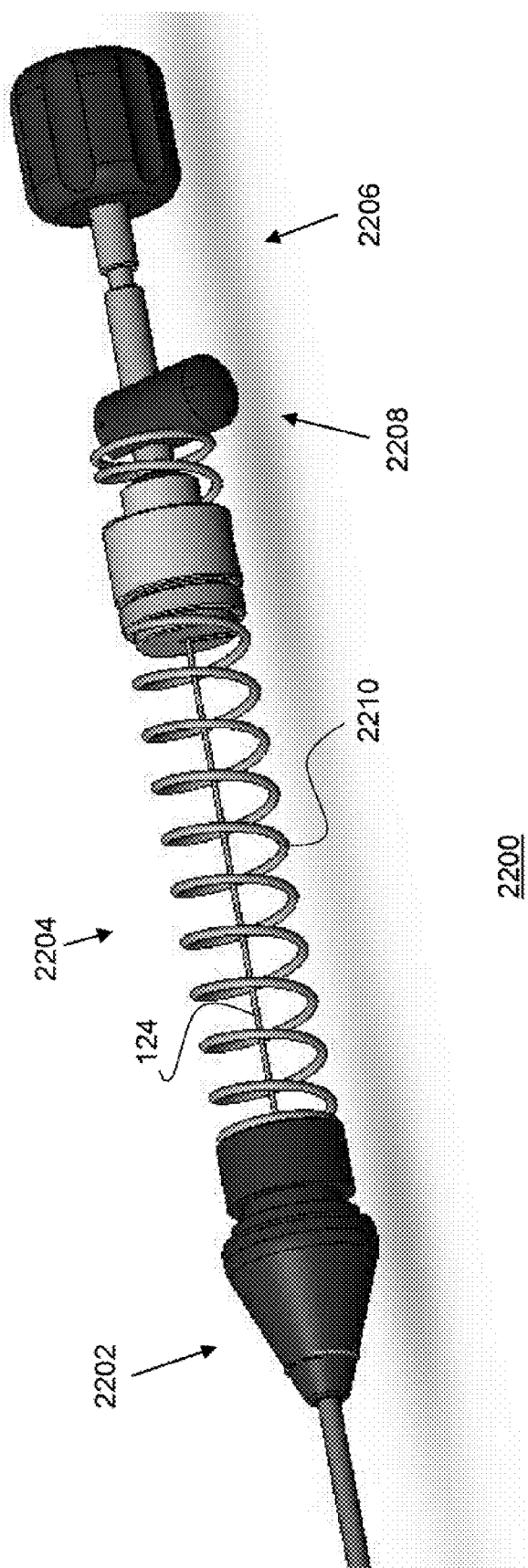
FIG. 22 is a perspective view of a handle at a proximal end of the retractor according to the invention in a retracted position.

FIG. 22 shows a handle 2200 of the flexible tissue retractor 100, which is the actuation device that controls the extension and retraction of the needles 102a, 102b. The handle 2200 includes a nose assembly 2202, a handle assembly 2204, a push-rod assembly 2206, and a locking assembly 2208.

Referring now to FIG. 23, it can be seen that handle assembly 2204 includes a handle body 2300 (not shown in FIG. 22) surrounding the retraction spring 2210. The push-rod assembly 2206 is composed of a push-rod 2302 and a knob 2304.

The needle body 106 is secured and rotationally fixed to a piston 2320 that is itself rotationally fixed to the push-rod 2302, which is rotationally fixed to the knob 2304. The plunder is rotatable within the handle body 2300. An operator, therefore, by secure the handle body 2300 with one hand, is able to cause rotation of the needles 102a, 102b by simply rotating the knob 2304, which in turn rotates: the push-rod 2302, the piston 2320, needle body 106, swivel bushing 702, and the entire remaining distal end 118 of the device 100.

A button 2306 for locking the push rod 2302 is installed in a button hollow 2308, which is formed near the proximal end of the handle body 2300. The button 2306 is disposed upon a button spring 2310, which is also received in the button hollow 2308. The button 2306 has a transverse bore 2314 for receiving a catch pin 2312 therein. In an installed position, a contained space 2316, defined by the catch pin 2312 and the interior surface of the bore 2314 in the button 2306 enclose the push rod 2302 to, thereby, retain the button 2306 in the handle body 2300.

The push-rod 2302 is also formed with a circumferential catch pin groove 2318 used to capture the catch pin 2312 when the push-rod 2302 is pressed from a proximal position shown in FIG. 23 to a distal position shown in FIG. 26. In the proximal position, the needles 102a, 102b are retracted within the tip 1008 (FIG. 27) and, in the distal position, the needles 102a, 102b are extended out of the tip 1008 (FIG. 30). When the catch pin 2312 is within the groove 2318, the needles 102a, 102b are in the extended position and the knob 440 can only be moved slightly; such movement is permitted by the play created by the length of the groove 2318 along the longitudinal extent of the push-rod 2302. Because the needles 102a, 102b are held in the deployed position, the user is, then, free to let go of the handle without the fear of needle 102a, 102b retraction, and to use their hands for other surgical procedures until retraction of the needles 102a, 102b is desired. A user can selectively engage the button 2306 to capture the push-rod 2302 with the catch pin 2312 or allow the push-rod 2302 to move freely in the longitudinal direction by pressing the button 2306 to move the catch pin 2312 out of the way so that the groove 2318 does not engage the catch pin 2312. By pressing the button 2306 down, the catch-pin 2312 is forced out of the catch-pin groove 2318, thereby unlocking the push-rod 2302 and automatically retracting the needles 102a, 102b because the retraction spring 2210 imparts a proximally directed bias to the piston 2320. Accordingly, the locking function of the button 2306 can be said to selectively retain the needles 102a, 102b in a given position.

The push-rod 2302 is also provide with a plurality of additional intermediate circumferential catch pin grooves 2402, 2404, 2406, which are, in this embodiment, three in number.

The intermediate catch pin grooves 2402, 2404, 2406 advantageously allow the distal section 118 of the retractor 100 to rotate independent of the proximal section 120 and unencumbered by frictional forces when the needles 102a, 102b are retracted within the tip 1008. This feature is best explained by looking briefly to FIGS. 27-29. FIG. 27 shows that the needles 102a, 102b are in a retracted position. When in this position, as shown in FIG. 28, the distal stop 122 is pressed against the bushing 802 of the proximal stop 804 by the spring 2210. This contact between the distal stop 122 and the bushing 802 is a frictional force that resists rotation. In one embodiment, this force applied by the spring 2210 is approximately 6 lbs.

Of course, when the needles 102a, 102b are fully deployed, as shown in FIGS. 30-32, there is no friction between the distal stop 122 and the bushing 802 because they are not in contact with each other. Through utilization of the intermediate catch pin grooves 2402, 2404, 2406, removal or at least reduction of this frictional contact can be achieved without fully deploying the needles 102a, 102b.

Referring back to FIGS. 24 and 25, by pressing the knob 2304 distally, the catch pin 2312 catches in one of the plurality of intermediate pin grooves 2402, 2404, 2406 and "ratchets" to a position that sufficiently counters the frictional spring-imposed pressure from between the distal stop 122 and the bushing 802.

FIG. 36 shows the rotation joint 115 with a friction reducing washer 3600 inserted between the swivel bushing 702 and the swivel coil coupler 704.

Figure 38:
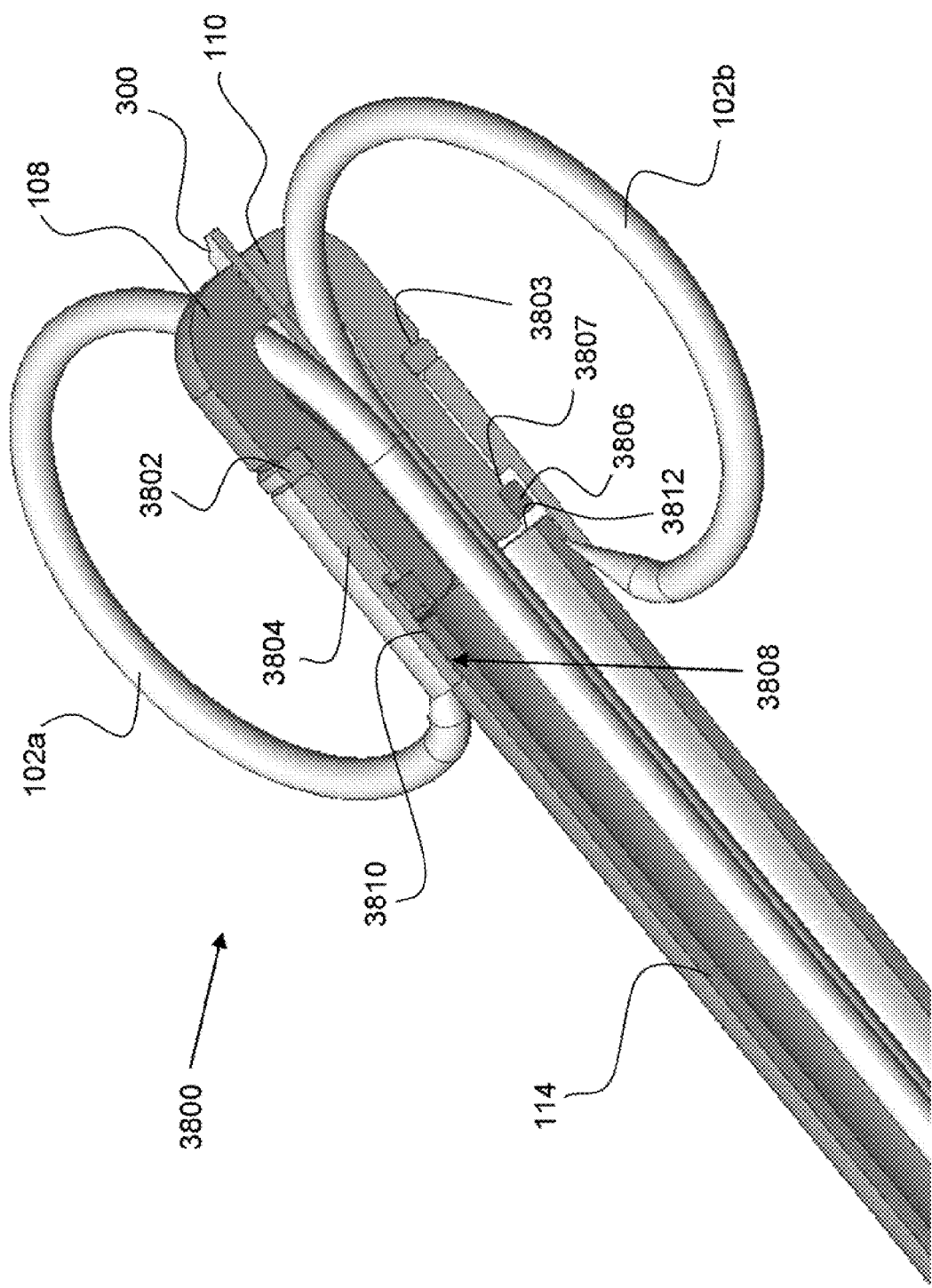
FIG. 38 is fragmentary, perspective, cross-sectional view of a distal end of the retractor of FIG. 1 in a needle deployed position, according to the invention.

FIG. 38 shows a cross-sectional perspective view of a distal tip 3800 that provides rotation of the needles 102a, 102b, according to an embodiment of the present invention. The distal tip 3800 includes the two head halves 108, 110 separated by the shim 300. In this embodiment, the head halves 108 and 110 are held in place by a distal ring 3802 that rests against a step 3803 formed in the head halves 108 and 110. The distal ring may or may not be affixed to the head halves 108, 110, but is made of a low-friction material, such as TEFLON, for instance. A sleeve 3800 is then slid over the head halves 108 and 110 and abuts the ring 3802. A second ring 3806 is then slid over a proximal portion of the head halves 108 and 110 and abuts a second step 3807 formed in the head halves 108 and 110. Then second ring 3806 is fixedly attached to the head halves 108 and 110 by, for instance, press fitting, welding, soldering, gluing, etc. in a way that prevents or resists the removal of the second ring 3806 from the head halves 108 and 110. The second ring 3806, thereby retains the sleeve 3804 and first ring 3802.

The proximal inner surface 3810 of the sleeve 3804 is then fixedly attached to the windings of the coil 114. The result is that the coil 114 and the sleeve 3804 remain fixed to each other while the second ring 3806, the head halves 108, 110, the needles 102a, 102b, and the shim 300 rotate with respect to the sleeve 3804 and coil 114. The first ring 3802 reduces friction between the head halves 108 and 110 and sleeve 3804. In this embodiment, the rotation joint 115 of FIG. 1 is not needed.

Other embodiments of the invention will be apparent to those skilled in the art from consideration of the specification and practice of the invention disclosed herein. It is intended that the specification and examples be considered as exemplary only.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

There have been described and illustrated herein several embodiments of retractors and methods for the endoluminal treatment of Gastroesophageal Reflux Disease (GERD). While particular embodiments of the invention have been described, it is not intended that the invention be limited thereto, as it is intended that the invention be as broad in scope as the art will allow and that the specification be read likewise. For example, while particular preferred dimensions have been provided for the retractor, it is appreciated that the system and its elements may have different relative sizes. For example, the cross-sectional areas can be decreased further if a pediatric endoscope (4 to 6 mm) is used. Also, while a "looking back" clip implantation instrument has been disclosed particularly for fastener application designed to treat GERD, it is appreciated that a "forward looking" straight instrument with similar jaw assembly can be used to apply the fastener for treatments of other conditions, e.g., obesity, ulceration, stomach cancer, implantation of pH measurement or monitoring devices, feeding tubes, etc. Moreover, a straight device can be smaller in diameter and be operated through a working channel of an endoscope. It will, therefore, be appreciated by those skilled in the art that yet other modifications could be made to the provided invention without deviating from its spirit and scope as so claimed.

What is claimed is:

1. A retractor for manipulating an object, the retractor comprising:
   a retractor body having proximal and distal ends;
   a retraction device having:
      a head connected at the distal end of the retractor body; and
      flexible needles of a shape memory material having a memory shape, at least one of the flexible needles having a needle body, the memory shape of the needles including a portion with an arcuate shape housed, at least partially, within the head;
   an actuation device connected to the proximal end of the retractor body and operatively connected to the needles, the actuation device, upon actuation thereof, moving the needles out of the head and withdrawing the needles into the head; and
   a rotation joint:
      having a slot shaped to accept a portion of the needle body;
      having at least one engaging surface corresponding to a surface of the needle body; and
      coupling the proximal end of the retractor body to the distal end of the retractor body and allowing the distal end of the retractor body and the retraction device to rotate independent of the proximal end of the retractor body, whereby rotation of the needle body causes rotation of the distal end of the retractor body and the flexible needles relative to the proximal end of the retractor body.

2. The retractor according to claim 1, wherein the actuation device comprises:
   a handle body; and
   a control knob rotationally freely coupled to the handle body and rotationally fixedly coupled to the needle body, wherein a rotation of the control knob results in rotation of the needles.

3. The retractor according to claim 2, wherein:
   the handle body has a distal end coupled to the proximal end of the retractor body and a proximal end coupled to the control knob.

4. The retractor according to claim 1, wherein the rotation joint comprises:
   a swivel bushing fixedly coupled to the distal end of the retractor body; and
   a swivel coil coupler fixedly coupled to the proximal end of the retractor body and rotationally freely coupled to the swivel bushing.

5. The retractor according to claim 1, wherein the distal end of the retractor body comprises: a distal coil surrounding a portion of the body of the at least one of the flexible needles, the distal coil having a plurality of windings and a plurality of winding coupling points at a distal end of the distal coil.

6. The retractor according to claim 1, wherein:
   the retractor body has a longitudinal extent defining a longitudinal direction; and
   the needles extend out of the head in a direction substantially orthogonal to said longitudinal direction.

7. The retractor according to claim 1, wherein:
   the head is integrally formed with the retractor body.

8. The retractor according to claim 1, wherein:
   the head defines channels for respective ones of the needles; and
   the channels have channel exits open to an environment.

9. The retractor according to claim 8, wherein:
   the retractor body has a longitudinal extent defining a longitudinal direction; and
   the channel exits open in a direction at an angle to the longitudinal direction.

10. The retractor according to claim 8, wherein:
    the channel exits are disposed on opposing sides of the head and the channels guide the needles through the channel exits.

11. The retractor according to claim 8, wherein: at least one surface of the channels guide the needles in a direction substantially orthogonal to a movement direction of a distal stop fixedly coupled to the needle body.

12. The retractor according to claim 1, wherein the head has two head halves clamping the needles therebetween.

13. The retractor according to claim 12, wherein the two head halves are removably connected to one another.

14. The retractor according to claim 12, wherein the head has a shim disposed between the two head halves.

15. The retractor according to claim 12, wherein said two head halves and a shim disposed between the two head halves define channels for respective ones of the needles.

16. A retractor for manipulating an object, the retractor comprising:
    a retractor body having proximal and distal ends;
    a retraction device having:
       a head connected at the distal end of the retractor body; and
       flexible needles of a shape memory material having a memory shape, the memory shape of the needles including a portion with an arcuate shape housed, at least partially, within the head;
    an actuation device connected to the proximal end of the retractor body and operatively connected to the needles, the actuation device, upon actuation thereof, moving the needles out of the head and withdrawing the needles into the head; and
    a rotation joint coupling the proximal end of the retractor body to the distal end of the retractor body and allowing the distal end of the retractor body and the retraction device to rotate independent of the proximal end of the retractor body, wherein the rotation joint comprises:
       a swivel bushing fixedly coupled to the distal end of the retractor body, the swivel bushing comprising a slot accepting a portion of a needle body and having at least one engaging surface corresponding to a flat surface of the needle body, the engaging surface of the swivel bushing and the flat surface of the needle body allowing a rotation of the needle body to generate a corresponding rotation of the swivel bushing; and a swivel coil coupler fixedly coupled to the proximal end of the retractor body and rotationally freely coupled to the swivel bushing.

17. The retractor according to claim 16, further comprising:

a distal stop fixedly coupled to the needle body and limiting an amount of lateral movement of the needle body through the swivel bushing.

18. The retractor according to claim 17, wherein:

the distal stop is between the rotation joint and the retraction device.

19. The retractor according to claim 17, wherein:

the distal stop has a dimension greater than a dimension of the slot thereby preventing movement of the needle body when the distal stop contacts the swivel bushing.

20. A retractor for manipulating an object, the retractor comprising:

a retractor body having proximal and distal ends;

a retraction device having:

a head connected at the distal end of the retractor body; and flexible needles of a shape memory material having a memory shape, at least one of the flexible needles having a needle body with at least one engaging surface, the memory shape of the needles including a portion with an arcuate shape housed, at least partially, within the head;

an actuation device connected to the proximal end of the retractor body and operatively connected to the needles, the actuation device, upon actuation thereof, moving the needles out of the head and withdrawing the needles into the head; and a rotation joint:

having a slot shaped to accept a portion of the needle body;

having at least one engaging surface corresponding to the at least one engaging surface of the needle body; and coupling the proximal end of the retractor body to the distal end of the retractor body and allowing the distal end of the retractor body and the retraction device to rotate independent of the proximal end of the retractor body, whereby the engaging surface of the rotation joint and the engaging surface of the needle body cooperate to allow a rotation of the needle body to cause a rotation of the distal end of the retractor body and the flexible needles relative to the proximal end of the retractor body.

* * * * *